US009738903B2

(12) United States Patent
Brown et al.

(10) Patent No.: US 9,738,903 B2
(45) Date of Patent: Aug. 22, 2017

(54) TRANSGENIC BRASSICA EVENT MON 88302 AND METHODS OF USE THEREOF

(71) Applicant: Monsanto Technology LLC, St. Louis, MO (US)

(72) Inventors: Andrew J. Brown, St. Louis, MO (US); James F. Byrne, Sacramento, CA (US); Robert H. Cole, Florissant (MO); James H. Crowley, Manchester, MO (US); John A. Miklos, Des Peres, MO (US); Robert C. Ripley, Saskatoon (CA); Simone Seifert-Higgins, House Springs, MO (US); Jiali Xie, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 448 days.

(21) Appl. No.: 14/333,479

(22) Filed: Jul. 16, 2014

(65) Prior Publication Data

US 2014/0373190 A1    Dec. 18, 2014

Related U.S. Application Data

(62) Division of application No. 13/151,082, filed on Jun. 1, 2011, now Pat. No. 8,816,156.

(60) Provisional application No. 61/351,317, filed on Jun. 4, 2010.

(51) Int. Cl.
*C12N 15/82* (2006.01)
*C12N 15/52* (2006.01)
*A01H 5/10* (2006.01)
*A01N 57/20* (2006.01)

(52) U.S. Cl.
CPC ......... *C12N 15/8275* (2013.01); *A01N 57/20* (2013.01)

(58) Field of Classification Search
None
See application file for complete search history.

(56) References Cited

U.S. PATENT DOCUMENTS

| 5,558,071 | A | 9/1996 | Ward et al. |
| 6,579,851 | B2 | 6/2003 | Goeke et al. |
| 6,613,963 | B1 * | 9/2003 | Gingera .................... A01H 5/00 435/418 |
| 7,566,817 | B2 | 7/2009 | Beazley et al. |
| 7,632,985 | B2 | 12/2009 | Malven et al. |
| 8,461,129 | B2 | 6/2013 | Bolduc et al. |
| 8,501,407 | B2 | 8/2013 | Brinker et al. |
| 2002/0144304 | A1 | 10/2002 | Fincher et al. |
| 2006/0282915 | A1 | 12/2006 | Malven et al. |
| 2008/0070260 | A1 | 3/2008 | Krieb et al. |
| 2011/0028412 | A1 | 2/2011 | Cappello et al. |
| 2011/0067141 | A1 | 3/2011 | Froman et al. |
| 2011/0067149 | A1 | 3/2011 | Wagner |
| 2013/0041004 | A1 | 2/2013 | Drager et al. |
| 2013/0084243 | A1 | 4/2013 | Goetsch et al. |
| 2013/0096073 | A1 | 4/2013 | Sidelman |
| 2014/0041075 | A1 | 2/2014 | Brinker et al. |
| 2014/0287922 | A1 | 9/2014 | Charne et al. |
| 2015/0119248 | A1 | 4/2015 | Brown et al. |
| 2016/0319299 | A1 | 11/2016 | Brinker et al. |

FOREIGN PATENT DOCUMENTS

| CN | 101170907 A | 10/2012 |
| JP | 2003-061577 | 3/2003 |
| JP | 2008-545413 | 12/2008 |
| WO | WO 02/30205 | 4/2002 |
| WO | WO 02/34946 | 5/2002 |
| WO | WO 02/36831 | 5/2002 |
| WO | WO 2004/072235 | 8/2004 |
| WO | WO 2006/096617 | 9/2006 |
| WO | WO 2006/128095 | 11/2006 |
| WO | WO 2006/130436 | 12/2006 |
| WO | WO 2007/015945 | 2/2007 |
| WO | WO 2010/036946 | 4/2010 |

OTHER PUBLICATIONS

Hohe et al, Plant Cell Rep. (2003) 21:1135-1142.*
English Translation of Japanese Office Action regarding Application No. 2013-513283, dated Nov. 10, 2015.
Response to Final Office Action regarding U.S. Appl. No. 14/595,093, dated Nov. 30, 2015.
Anonymous, "Late Weed Spray Costs in More Ways Than One," accessed on Nov. 30, 2015, from <<www.canolawatch.org/2013/06/12/late-weed-spray-costs-in-more-ways-than-one>>, dated 2013.
Harker, "Integrated Weed Management in a HT Canola World," downloaded Nov. 23, 2015, from <<http://umanitoba.ca/faculties/afs/MAC_proceedings/proceedings/2010/Neil_Harker.pdf>>, 2010.
Anonymous, "How Late Can You Spray," accessed on Nov. 30, 2015, from <<www.canolawatch.org/2010/06/23/how-late-can-you-spray>>, dated 2010.
USPTO: Non-Final Office Action regarding U.S. Appl. No. 14/595,093, dated Jan. 14, 2016.
Response to non-final Office Action regarding U.S. Appl. No. 14/595,093, dated Apr. 11, 2016.
Shilling et al., "Glyphosate Can Reduce Glyphosate-Resistant Canola Growth After Individual or Sequential Applications," Weed Technology 20:825-830, 2006.
USPTO: Final Office Action regarding U.S. Appl. No. 14/595,093, dated Apr. 29, 2016.
U.S. Appl. No. 13/945,741, filed Jul. 18, 2013, Brinker et al.
U.S. Appl. No. 14/179,524, filed Feb. 12, 2014, Froman et al.
New England BioLabs Inc. 1998/99 Catalog, (NEB Catalog), pp. 121 and 284, undated.

(Continued)

*Primary Examiner* — Mykola V Kovalenko
(74) *Attorney, Agent, or Firm* — Dentons US LLP; Pamela Sisson

(57) ABSTRACT

The invention provides plants comprising transgenic event MON 88302 that exhibit tolerance to glyphosate herbicide. The invention also provides seeds, plant parts, cells, commodity products, and methods related to the event. The invention also provides DNA molecules that are unique to the event and were created by the insertion of transgenic DNA into the genome of a *Brassica napus* plant.

21 Claims, 3 Drawing Sheets

(56) References Cited

OTHER PUBLICATIONS

USPTO: Final Office Action regarding U.S. Appl. No. 11/801,114, dated Aug. 26, 2009.
Cajacob et al., "Engineering resistance to herbicides," In: P. Christou and H. Klee: *Handbook of Plant Biotechnology*, pp. 353-372, Jul. 15, 2004.
Cajacob et al., "Genetically modified herbicide resistant crops," In: W. Kramer and U. Schirmer: *Modern Crop Protection Compounds*, pp. 283-316, Jan. 1, 2007.
Dill et al., "Glyphosate-resistant crops: adoption, use, and future considerations," *Pest Management Science* 64(4):326-331, 2008.
Feng et al., "Glyphosate-resistant crops: developing the next generation products," In: Vijay Nandula: *Glyphosate Resistance in Crops and Weeds: History, Development, and Management*, pp. 45-65, Jul. 21, 2010.
Green et al., "Evolution of glyphosate-resistant crop technology," *Weed Science* 57(1):108-117, 2009.
Taverniers et al., "Event-specific plasmid standards and real-time PCR methods for transgenic Bt11, Bt176, and GA21 maize and transgenic GT73 canola," *Journal of Agricultural and Food Chemistry* 53(8):3041-3052, 2005.
USPTO: Non-Final Office Action regarding U.S. Appl. No. 12/865,844, dated Jun. 20, 2013.
Alignment of SEQ ID No. 1 from U.S. Appl. No. 13/151,082 and SEQ ID No. 1 from U.S. Appl. No. 13/945,741, undated.
Response to Non-Final Office Action regarding U.S. Appl. No. 12/865,844, dated Sep. 17, 2013.
Notice of Allowance issued in U.S. Appl. No. 12/865,844, dated Nov. 19, 2013.
Sequence alignment information as indicated in transmittal letter of Nov. 25, 2013 Information Disclosure Statement for U.S. Appl. No. 13/151,082.
Genbank Accession No. BX891430, dated Oct. 10, 2003.
Hohe et al., "A tool for understanding homologous recombination in plants," *Plant Cell Rep.* 21:1135-1142, 2003.
USPTO: Final Office Action regarding U.S. Appl. No. 14/595,093, dated Aug. 31, 2015.
Nandula et al., "Glyphosate-Resistant and -Susceptible Soybean (*Glycine max*) and Canola (*Brassica napus*) Dose Response and Metabolism Relationships with Glyphosate," *J. Agric. Food Chem.* 55:3540-3545, 2007.
Third-Party Submission regarding U.S. Appl. No. 14/595,093, dated Aug. 17, 2015.
Bernhard et al., "Petition for the Determination of Nonregulated Status for Glyphosate-Tolerant Canola MON 88302," pp. 1-502, dated Jun. 27, 2011.
USPTO: Final Office Action regarding U.S. Appl. No. 13/151,082, dated Mar. 6, 2014.
Response to Non-Final Office Action regarding U.S. Appl. No. 14/595,093, dated Jun. 4, 2015.
U.S. Appl. No. 14/595,093, filed Jan. 12, 2015, Brown et al.
Clayton et al., "Glyphosate Timing and Tillage System Effects on Glyphosate-Resistant Canola (*Brassica napus*)," *Weed Technology* 16:124-130, 2002.
Grey et al., "Herbicide-Resistant Canola (*Brassica napus*) Response and Weed Control with Postemergence Herbicides," *Weed Technology* 20:551-557, 2006.
Xiangxiang et al., "Assessment on alien herbicide-resistant gene flow among crucifers by sexual compatibility," *Chinese Science Bulletin* 50:1604-1611, 2005.
USPTO: Non-Final Office Action regarding U.S. Appl. No. 14/595,093, dated Mar. 6, 2015.
Anklam et al., "Analytical methods for detection and determination of genetically modified organisms in agricultural crops and plant-derived food products," *Eur. Food Res. Technol.* 214:3-26, 2002.
Carrington et al., "Cap-Independent Enhancement of Translation by a Plant Potyvirus 5' Nontranslated Region," *Journal of Virology* 64(4):1590-1597, 1990.
Rosso et al., "An *Arabidopsis thaliana* T-DNA mutagenized population (GABI-Kat) for flanking sequence tag-based reverse genetics," *Plant Molecular Biology* 53:247-259, 2003.
Appeal Brief regarding U.S. Appl. No. 14/595,093, dated Dec. 27, 2016.
USPTO: Examiner's Answer to Appeal Brief regarding U.S. Appl. No. 14/595,093, dated Apr. 21, 2017.
Reply Brief regarding U.S. Appl. No. 14/595,093, dated Jun. 21, 2017.

\* cited by examiner

SEQUENCE LISTING

```
<160> NUMBER OF SEQ ID NOS: 19

<210> SEQ ID NO 1
<211> LENGTH: 60
<212> TYPE: DNA
<213> ORGANISM: Artificial Sequence
<220> FEATURE:
<223> OTHER INFORMATION: Chimeric DNA molecule of Canola genomic DNA and
      transgene DNA

<400> SEQUENCE: 1 aaaccttta gtcatcatgt tgtaccactt caaacactga tagtttaaac tgaaggcggg        60

<210> SEQ ID NO 2
<211> LENGTH: 60
<212> TYPE: DNA
<213> ORGANISM: Artificial Sequence
<220> FEATURE:
<223> OTHER INFORMATION: Chimeric DNA molecule of Canola gemonic DNA and
      transgene DNA

<400> SEQUENCE: 2
tttcccggac atgaagccat ttacaattga ccatcatact caacttcaat tttttttaat        60

<210> SEQ ID NO 3
<211> LENGTH: 956
<212> TYPE: DNA
<213> ORGANISM: Artificial Sequence
<220> FEATURE:
<223> OTHER INFORMATION: Chimeric DNA molecule of Canola genomic DNA and
      transgene DNA

<400> SEQUENCE: 3
ttatctatct tttttgtag gtcctaataa acgggctaca gcactttgtg ccaacaaagg         60
```

```
tgaagccaaa gttacagata gtcgaaacat ttatcaaggt aagcaaacca gaaactcata    120
tgaaagtata gcagacttga gatcataata tgctggtgat acacacttaa aaatcggaat    180
catcactcat tttttttgca ggcatactat ctgccagaga cggaatatgt ccactgggca    240
agagctcatc cggtaaacaa acaaatcttt cttaatcttt cttaatcttt ataatgtttt    300
gcgtaaatta aatcgatggg atagaagact aatatgatta aaatgtgtaa acatacagga    360 atatcgaaa gcacaggtca ttggacttgt gaatttagta gccaccatga aaagctggaa     420
gaggaaaacg cgtctagaag ttgtggataa gattgaatca gctgctgcat agatcaaatc    480
taaaagcaac aacaaagtaa tttttttact tcttttctct ggtcttgttc tgtctttgct    540
tttggctctt acttttgcgt tttgaaccga gtgtgtaaat ttgaggataa gcccttctta    600
gttatcatct ttcttttgct taatgggggtt tgtgtaaaag atcctcctca agttgtacag   660
tcttgaagag attgtaacac acggtttcct acatttaaat acttaattaa tgtctcagta    720
tttgtattat cagttccttg aaccttattt tatagtgcac aaaacctttt agtcatcatg    780
ttgtaccact tcaaacactg atagtttaaa ctgaaggcgg gaaacgacaa tctgatcccc    840
atcaagctct agctagagcg gccgcgttat caagcttctg caggtcctgc tcgagtggaa    900
gctaattctc agtccaaagc ctcaacaagg tcagggtaca gagtctccaa accatt        956

<210> SEQ ID NO 4
<211> LENGTH: 1250
<212> TYPE: DNA
<213> ORGANISM: Artificial Sequence
<220> FEATURE:
<223> OTHER INFORMATION: Chimeric DNA molecule of Canola genomic DNA
      and transgene DNA

<400> SEQUENCE: 4
caattgattg acaacatgca tcaatcgacc tgcagccact cgaagcggcc gcatcgatcg      60
tgaagtttct catctaagcc cccatttgga cgtgaatgta gacacgtcga aataaagatt    120
tccgaattag aataatttgt ttattgcttt cgcctataaa tacgacggat cgtaatttgt    180
cgttttatca aaatgtactt tcatttttata ataacgctgc ggacatctac attttttgaat  240 tgaaaaaaaa ttggtaatta ctctttcttt ttctccatat tgaccatcat actcattgct    300
gatccatgta gatttcccgg acatgaagcc atttacaatt gaccatcata ctcaacttca    360 attttttta atgtcattat gatagatgaa taattccttt tcttatcctg ttgaccataa     420
taatgataaa acagtaatca tgataaatat atcaaaaagt gtattttaaa aattttctaa    480
tcattattcg agaaaaaaaa caaatcattt gtaagtttca ctgttaacta cagatgaaac    540 atctttttgtt tttaacgttt taatgatatt gaaatcaatc agaataaaag gtgtctcatc    600
tcttgtgtac tgtcatgttt gcgatgagag gctggaagaa agactagtca aaagacttca    660
aagctgtggt gatttagttg tatctccaac cattttttaat gcaacgcatg gttcatctac    720
tggtacctgt tgcacaataa acattcaaa acatgttat tttacaaatc ttcactaaaa       780
gccttcaatt tcatatgatg cgtgtcaatg taaaccgact tcttattttc aaactgttga    840
tgtgaaagag agaaaaaaat cagagaagta aaatttatga aggagattta ctaagaagta    900
aattgtttta taaataatta ttttttatata aaataagatt tattattatt ttttcatgtt   960
aatgttaaaa gaccttttaaa aaatatgcat tacgttttta taacagtaga gatgttttta  1020
agaattgata ttaggtagct ttttaaaatt aatttagtaa ttatctaaaa aaaatgatct   1080 ctttttataaa aagaaaaaat cacagagatc cagatactgt cgtgtgaagt attaaagaga  1140
```

| | |
|---|---|
| tgtctttaaa aagtattaaa gagacagtcg acagtttgct atctgttgta ataaataata | 1200 |
| gaaaaataaa gaaactgcag caggaagata aagaaaacat gagagacata | 1250 |

<210> SEQ ID NO 5
<211> LENGTH: 4427
<212> TYPE: DNA
<213> ORGANISM: Artificial Sequence
<220> FEATURE:
<223> OTHER INFORMATION: Transgene insert

<400> SEQUENCE: 5

| | |
|---|---|
| caaacactga tagtttaaac tgaaggcggg aaacgacaat ctgatcccca tcaagctcta | 60 |
| gctagagcgg ccgcgttatc aagcttctgc aggtcctgct cgagtggaag ctaattctca | 120 |
| gtccaaagcc tcaacaaggt cagggtacag agtctccaaa ccattagcca aaagctacag | 180 |
| gagatcaatg aagaatcttc aatcaaagta aactactgtt ccagcacatg catcatggtc | 240 |
| agtaagtttc agaaaaagac atccaccgaa gacttaaagt tagtgggcat ctttgaaagt | 300 |
| aatcttgtca acatcgagca gctggcttgt ggggaccaga caaaaaagga atggtgcaga | 360 |
| attgttaggc gcacctacca aaagcatctt tgcctttatt gcaaagataa agcagattcc | 420 |
| tctagtacaa gtggggaaca aaataacgtg aaaagagct gtcctgacag cccactcact | 480 |
| aatgcgtatg acgaacgcag tgacgaccac aaaagaatta gcttgagctc aggatttagc | 540 |
| agcattccag attgggttca atcaacaagg tacgagccat atcactttat tcaaattggt | 600 |
| atcgccaaaa ccaagaagga actcccatcc tcaaaggttt gtaaggaaga attcgatatc | 660 |
| aagcttgata tcggaagttt ctctcttgag ggaggttgct cgtggaatgg acacatatg | 720 |
| gttgttataa taaccatttt ccattgtcat gagattttga ggttaatata tactttactt | 780 |
| gttcattatt ttatttggtg tttgaataaa tgatataaat ggctcttgat aatctgcatt | 840 |
| cattgagata tcaaatattt actctagaga agagtgtcat atagattgat ggtccacaat | 900 |
| caatgaaatt tttgggagac gaacatgtat aaccatttgc ttgaataacc ttaattaaaa | 960 |
| ggtgtgatta aatgatgttt gtaacatgta gtactaaaca ttcataaaac acaaccaacc | 1020 |
| caagaggtat tgagtattca cggctaaaca ggggcataat ggtaatttaa agaatgatat | 1080 |
| tatttatgt taaaccctaa cattggtttc ggattcaacg ctataaataa aaccactctc | 1140 |
| gttgctgatt ccatttatcg ttcttattga ccctagccgc tacacacttt tctgcgatat | 1200 |
| ctctgaggta agcgttaacg taccttaga tcgttctttt tcttttttcgt ctgctgatcg | 1260 |
| ttgctcatat tatttcgatg attgttggat tcgatgctct ttgttgattg atcgttctga | 1320 |
| aaattctgat ctgttgttta gatttttatcg attgttaata tcaacgtttc actgcttcta | 1380 |
| aacgataatt tattcatgaa actatttttcc cattctgatc gatcttgttt tgagattta | 1440 |
| atttgttcga ttgattgttg gttggtggat ctatatacga gtgaacttgt tgatttgcgt | 1500 |
| atttaagatg tatgtcgatt tgaattgtga ttgggtaatt ctggagtagc ataacaaatc | 1560 |
| cagtgttccc tttttctaag ggtaattctc ggattgtttg ctttatatct cttgaaattg | 1620 |
| ccgatttgat tgaatttagc tcgcttagct cagatgatag agcaccacaa ttttttgtggt | 1680 |
| agaaatcggt ttgactccga tagcggcttt ttactatgat tgttttgtgt taagatgat | 1740 |
| tttcataatg gttatatatg tctactgttt ttattgattc aatatttgat tgttctttt | 1800 |
| tttgcagatt tgttgaccag agatctacca tggcgcaagt tagcagaatc tgcaatggtg | 1860 |
| tgcagaaccc atctcttatc tccaatctct cgaaatccag tcaacgcaaa tctcccttat | 1920 |

```
cggtttctct gaagacgcag cagcatccac gagcttatcc gatttcgtcg tcgtggggat    1980
tgaagaagag tgggatgacg ttaattggct ctgagcttcg tcctcttaag gtcatgtctt    2040
ctgtttccac ggcgtgcatg cttcacggtg caagcagccg tccagcaact gctcgtaagt    2100
cctctggtct ttctggaacc gtccgtattc caggtgacaa gtctatctcc cacaggtcct    2160
tcatgtttgg aggtctcgct agcggtgaaa ctcgtatcac cggtcttttg gaaggtgaag    2220
atgttatcaa cactggtaag gctatgcaag ctatgggtgc cagaatccgt aaggaaggtg    2280
atacttggat cattgatggt gttggtaacg gtggactcct tgctcctgag gctcctctcg    2340
atttcggtaa cgctgcaact ggttgccgtt tgactatggg tcttgttggt gtttacgatt    2400
tcgatagcac tttcattggt gacgcttctc tcactaagcg tccaatgggt cgtgtgttga    2460
acccacttcg cgaaatgggt gtgcaggtga agtctgaaga cggtgatcgt cttccagtta    2520
ccttgcgtgg accaaagact ccaacgccaa tcacctacag ggtacctatg gcttccgctc    2580
aagtgaagtc cgctgttctg cttgctggtc tcaacacccc aggtatcacc actgttatcg    2640
agccaatcat gactcgtgac cacactgaaa agatgcttca aggttttggt gctaacctta    2700
ccgttgagac tgatgctgac ggtgtgcgta ccatccgtct tgaaggtcgt ggtaagctca    2760
ccggtcaagt gattgatgtt ccaggtgatc catcctctac tgctttccca ttggttgctg    2820
ccttgcttgt tccaggttcc gacgtcacca tccttaacgt tttgatgaac ccaacccgta    2880
ctggtctcat cttgactctg caggaaatgg gtgccgacat cgaagtgatc aacccacgtc    2940
ttgctggtgg agaagacgtg gctgacttgc gtgttcgttc ttctactttg aagggtgtta    3000
ctgttccaga gaccgtgct ccttctatga tcgacgagta tccaattctc gctgttgcag    3060
ctgcattcgc tgaaggtgct accgttatga cggtttgga agaactccgt gttaaggaaa    3120
gcgaccgtct ttctgctgtc gcaaacggtc tcaagctcaa cggtgttgat tgcgatgaag    3180
gtgagacttc tctcgtcgtg cgtggtcgtc ctgacggtaa gggtctcggt aacgcttctg    3240
gagcagctgt cgctacccac ctcgatcacc gtatcgctat gagcttcctc gttatgggtc    3300
tcgtttctga aaaccctgtt actgttgatg atgctactat gatcgctact agcttcccag    3360
agttcatgga tttgatggct ggtcttggag ctaagatcga actctccgac actaaggctg    3420
cttgatgagc tcaagaattc gagctcggta ccggatcctc tagctagagc tttcgttcgt    3480
atcatcggtt tcgacaacgt tcgtcaagtt caatgcatca gtttcattgc gcacacacca    3540
gaatcctact gagtttgagt attatggcat tgggaaaact gttttcttg taccatttgt    3600 tgtgcttgta atttactgtg tttttattc ggttttcgct atcgaactgt gaaatggaaa    3660
tggatggaga agagttaatg aatgatatgg tcctttgtt cattctcaaa ttaatattat    3720
ttgttttttc tcttattgt tgtgtgttga atttgaaatt ataagagata tgcaaacatt    3780
ttgttttgag taaaaatgtg tcaaatcgtg gcctctaatg accgaagtta atatgaggag    3840
taaaacactt gtagttgtac cattatgctt attcactagg caacaaatat attttcagac    3900
ctagaaaagc tgcaaatgtt actgaataca agtatgtcct cttgtgtttt agacatttat    3960
gaactttcct ttatgtaatt ttccagaatc cttgtcagat tctaatcatt gctttataat    4020
tatagttata ctcatggatt tgtagttgag tatgaaaata ttttttaatg cattttatga    4080
cttgccaatt gattgacaac atgcatcaat cgacctgcag ccactcgaag cggccgcatc    4140
gatcgtgaag tttctcatct aagccccat ttggacgtga atgtagacac gtcgaaataa    4200
agatttccga attagaataa tttgtttatt gctttcgcct ataaatacga cggatcgtaa    4260
tttgtcgttt tatcaaaatg tactttcatt ttataataac gctgcggaca tctacatttt    4320
```
tgaattgaaa aaaaattggt aattactctt tcttttctc catattgacc atcatactca    4380
ttgctgatcc atgtagattt cccggacatg aagccattta caattga                 4427

<210> SEQ ID NO 6
<211> LENGTH: 6126
<212> TYPE: DNA
<213> ORGANISM: Artificial Sequence
<220> FEATURE:
<223> OTHER INFORMATION: Chimeric DNA molecule of Canola genomic DNA
      and transgene DNA

<400> SEQUENCE: 6
ttatctatct ttttttgtag gtcctaataa acgggctaca gcactttgtg ccaacaaagg      60
tgaagccaaa gttacagata gtcgaaacat ttatcaaggt aagcaaacca gaaactcata    120
tgaaagtata gcagacttga gatcataata tgctggtgat acacacttaa aaatcggaat    180
catcactcat ttttttgca ggcatactat ctgccagaga cggaatatgt ccactgggca    240
agagctcatc cggtaaacaa acaaatcttt cttaatcttt cttaatcttt ataatgtttt    300
gcgtaaatta aatcgatggg atagaagact aatatgatta aatgtgtaa acatacagga    360 atatacgaaa gcacaggtca ttggacttgt gaatttagta gccaccatga aaagctggaa    420
gaggaaaacg cgtctagaag ttgtggataa gattgaatca gctgctgcat agatcaaatc    480
taaaagcaac aacaaagtaa ttttttact tcttttctct ggtcttgttc tgtctttgct    540
tttggctctt acttttgcgt tttgaaccga gtgtgtaaat ttgaggataa gcccttctta    600
gttatcatct ttcttttgct taatgggggtt tgtgtaaaag atcctcctca agttgtacag    660
tcttgaagag attgtaacac acggtttcct acatttaaat acttaattaa tgtctcagta    720
tttgtattat cagttccttg aaccttattt tatagtgcac aaaaccttt agtcatcatg    780 ttgtaccact tcaaacactg atagtttaaa ctgaaggcgg gaaacgacaa tctgatcccc    840
atcaagctct agctagagcg gccgcgttat caagcttctg caggtcctgc tcgagtggaa    900
gctaattctc agtccaaagc ctcaacaagg tcagggtaca gagtctccaa accattagcc    960
aaaagctaca ggagatcaat gaagaatctt caatcaaagt aaactactgt tccagcacat   1020
gcatcatggt cagtaagttt cagaaaaaga catccaccga agacttaaag ttagtgggca   1080
tctttgaaag taatcttgtc aacatcgagc agctggcttg tggggaccag acaaaaaagg   1140
aatggtgcag aattgttagg cgcacctacc aaaagcatct ttgcctttat tgcaaagata   1200
aagcagattc ctctagtaca agtggggaac aaaataacgt ggaaaagagc tgtcctgaca   1260
gcccactcac taatgcgtat gacgaacgca gtgacgacca caaaagaatt gcttgagct    1320 caggatttag cagcattcca gattgggttc aatcaacaag gtacgagcca tatcacttta   1380
ttcaaattgg tatcgccaaa accaagaagg aactcccatc ctcaaaggtt tgtaaggaag   1440
aattcgatat caagcttgat atcggaagtt tctctcttga gggaggttgc tcgtggaatg   1500
ggacacatat ggttgttata ataaaccatt tccattgtca tgagattttg aggttaatat   1560
atactttact tgttcattat tttatttggt gtttgaataa atgatataaa tggctcttga   1620
taatctgcat tcattgagat atcaaatatt tactctagag aagagtgtca tatagattga   1680
tggtccacaa tcaatgaaat ttttgggaga cgaacatgta taaccatttg cttgaataac   1740
cttaattaaa aggtgtgatt aaatgatgtt tgtaacatgt agtactaaac attcataaaa   1800
cacaaccaac ccaagaggta ttgagtattc acggctaaac aggggcataa tggtaattta   1860
aagaatgata ttatttttatg ttaaacccta acattggttt cggattcaac gctataaata   1920

```
aaaccactct cgttgctgat tccatttatc gttcttattg accctagccg ctacacactt    1980
ttctgcgata tctctgaggt aagcgttaac gtacccttag atcgttcttt ttcttttcg    2040
tctgctgatc gttgctcata ttatttcgat gattgttgga ttcgatgctc tttgttgatt    2100
gatcgttctg aaaattctga tctgttgttt agatttatc gattgttaat atcaacgttt    2160
cactgcttct aaacgataat ttattcatga aactattttc ccattctgat cgatcttgtt    2220
ttgagatttt aatttgttcg attgattgtt ggttggtgga tctatatacg agtgaacttg    2280
ttgatttgcg tatttaagat gtatgtcgat ttgaattgtg attgggtaat tctggagtag    2340
cataacaaat ccagtgttcc cttttctaa gggtaattct cggattgttt gctttatatc    2400
tcttgaaatt gccgatttga ttgaatttag ctcgcttagc tcagatgata gagcaccaca    2460
attttttgtgg tagaaatcgg tttgactccg atagcggctt tttactatga ttgttttgtg    2520
ttaaagatga ttttcataat ggttatatat gtctactgtt tttattgatt caatatttga    2580
ttgttctttt ttttgcagat ttgttgacca gagatctacc atggcgcaag ttagcagaat    2640
ctgcaatggt gtgcagaacc catctcttat ctccaatctc tcgaaatcca gtcaacgcaa    2700
atctcccta tcggtttctc tgaagacgca gcagcatcca cgagcttatc cgatttcgtc    2760
gtcgtgggga ttgaagaaga gtgggatgac gttaattggc tctgagcttc gtcctcttaa    2820
ggtcatgtct tctgttttcca cggcgtgcat gcttcacggt gcaagcagcc gtccagcaac    2880
tgctcgtaag tcctctggtc tttctggaac cgtccgtatt ccaggtgaca gtctatctc    2940
ccacaggtcc ttcatgtttg gaggtctcgc tagcggtgaa actcgtatca ccggtctttt    3000
ggaaggtgaa gatgttatca acactggtaa ggctatgcaa gctatgggtg ccagaatccg    3060
taaggaaggt gatacttgga tcattgatgg tgttggtaac ggtggactcc ttgctcctga    3120
ggctcctctc gatttcggta acgctgcaac tggttgccgt ttgactatgg gtcttgttgg    3180
tgtttacgat ttcgatagca cttcattgg tgacgcttct ctcactaagc gtccaatggg    3240
tcgtgtgttg aacccacttc gcgaaatggg tgtgcaggtg aagtctgaag acggtgatcg    3300
tcttccagtt accttgcgtg gaccaaagac tccaacgcca atcacctaca gggtaccat    3360
ggcttccgct caagtgaagt ccgctgttct gcttgctggt ctcaacaccc caggtatcac    3420
cactgttatc gagccaatca tgactcgtga ccacactgaa aagatgcttc aaggttttgg    3480
tgctaacctt accgttgaga ctgatgctga cggtgtgcgt accatccgtc ttgaaggtcg    3540
tggtaagctc accggtcaag tgattgatgt tccaggtgat ccatcctcta ctgctttccc    3600
attggttgct gccttgcttg ttccaggttc cgacgtcacc atccttaacg ttttgatgaa    3660
cccaacccgt actggtctca tcttgactct gcaggaaatg ggtgccgaca tcgaagtgat    3720
caacccacgt cttgctggtg gagaagacg ggctgacttg cgtgttcgtt cttctacttt    3780
gaagggtgtt actgttccag aagaccgtgc tccttctatg atcgacgagt atccaattct    3840
cgctgttgca gctgcattcg ctgaaggtgc taccgttatg aacggtttgg aagaactccg    3900
tgttaaggaa agcgaccgtc tttctgctgt cgcaaacggt ctcaagctca cggtgttga    3960
ttgcgatgaa ggtgagactt ctctcgtcgt gcgtggtcgt cctgacgtta agggtctcgg    4020
taacgcttct ggagcagctg tcgctaccca cctcgatcac cgtatcgcta tgagcttcct    4080
cgttatgggt ctcgtttctg aaaaccctgt tactgttgat gatgctacta tgatcgctac    4140
tagcttccca gagttcatgg atttgatggc tggtcttgga gctaagatcg aactctccga    4200
cactaaggct gcttgatgag ctcaagaatt cgagctcggt accggatcct ctagctagag    4260
```

```
ctttcgttcg tatcatcggt ttcgacaacg ttcgtcaagt tcaatgcatc agtttcattg   4320
cgcacacacc agaatcctac tgagtttgag tattatggca ttgggaaaac tgttttcctt   4380
gtaccatttg ttgtgcttgt aatttactgt gtttttatt cggttttcgc tatcgaactg    4440
tgaaatggaa atggatggag aagagttaat gaatgatatg gtccttttgt tcattctcaa   4500
attaatatta tttgtttttt ctcttatttg ttgtgtgttg aatttgaaat tataagagat   4560
atgcaaacat tttgttttga gtaaaaatgt gtcaaatcgt ggcctctaat gaccgaagtt   4620
aatatgagga gtaaaacact tgtagttgta ccattatgct tattcactag gcaacaaata   4680
tattttcaga cctagaaaag ctgcaaatgt tactgaatac aagtatgtcc tcttgtgttt   4740
tagacattta tgaactttcc tttatgtaat tttccagaat ccttgtcaga ttctaatcat   4800
tgctttataa ttatagttat actcatggat ttgtagttga gtatgaaaat atttttaat    4860 gcatttatg acttgccaat tgattgacaa catgcatcaa tcgacctgca gccactcgaa    4920
gcggccgcat cgatcgtgaa gtttctcatc taagccccca tttggacgtg aatgtagaca   4980
cgtcgaaata aagatttccg aattagaata atttgtttat tgctttcgcc tataaatacg   5040
acggatcgta atttgtcgtt ttatcaaaat gtactttcat tttataataa cgctgcggac   5100
atctacattt ttgaattgaa aaaaaattgg taattactct ttcttttct ccatattgac    5160 catcatactc attgctgatc catgtagatt tcccggacat gaagccattt acaattgacc   5220
atcatactca acttcaattt tttttaatgt cattatgata gatgaataat tcctttttctt  5280 atcctgttga ccataataat gataaaacag taatcatgat aaatatatca aaaagtgtat   5340
tttaaaaatt ttctaatcat tattcgagaa aaaaaacaaa tcatttgtaa gtttcactgt   5400
taactacaga tgaaacatct tttgttttta acgttttaat gatattgaaa tcaatcagaa   5460
taaaaggtgt ctcatctctt gtgtactgtc atgtttgcga tgagaggctg gaagaaagac   5520
tagtcaaaag acttcaaagc tgtggtgatt tagttgtatc tccaaccatt tttaatgcaa   5580
cgcatggttc atctactggt acctgttgca caataaaaca ttcaaaaaca tgttatttta   5640
caaatcttca ctaaaagcct tcaatttcat atgatgcgtg tcaatgtaaa ccgacttctt   5700
attttcaaac tgttgatgtg aaagagagaa aaaaatcaga gaagtaaaat ttatgaagga   5760
gatttactaa gaagtaaatt gttttataaa taattatttt tatataaaat aagatttatt   5820
attatttttt catgttaatg ttaaaagacc tttaaaaaat atgcattacg ttttttataac  5880 agtagagatg ttttttaagaa ttgatattag gtagcttttt aaaattaatt tagtaattat  5940
ctaaaaaaaa tgatctcttt tataaaaaga aaaatcaca gagatccaga tactgtcgtg    6000
tgaagtatta aagagatgtc tttaaaaagt attaaagaga cagtcgacag tttgctatct   6060
gttgtaataa ataatagaaa aataaagaaa ctgcagcagg aagataaaga aaacatgaga   6120
gacata                                                              6126
```

<210> SEQ ID NO 7
<211> LENGTH: 100
<212> TYPE: DNA
<213> ORGANISM: Artificial Sequence
<220> FEATURE:
<223> OTHER INFORMATION: Chimeric DNA molecule of Canola genomic DNA
      and transgene DNA

<400> SEQUENCE: 7

```
accttatttt atagtgcaca aaaccttta gtcatcatgt tgtaccactt caaacactga    60
tagtttaaac tgaaggcggg aaacgacaat ctgatcccca                         100
```

```
<210> SEQ ID NO 8
<211> LENGTH: 100
<212> TYPE: DNA
<213> ORGANISM: Artificial Sequence
<220> FEATURE:
<223> OTHER INFORMATION: Chimeric DNA molecule of Canola genomic DNA
      and transgene DNA

<400> SEQUENCE: 8
tcattgctga tccatgtaga tttcccggac atgaagccat ttacaattga ccatcatact    60
caacttcaat ttttttttaat gtcattatga tagatgaata                        100

<210> SEQ ID NO 9
<211> LENGTH: 24
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 9
cattgctgat ccatgtagat ttcc                                           24

<210> SEQ ID NO 10
<211> LENGTH: 30
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 10
attaaaaaaa attgaagttg agtatgatgg                                     30

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
acatgaagcc atttacaatt                                                20

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
gctagagctt gatggggatc ag                                             22

<210> SEQ ID NO 13
<211> LENGTH: 28
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 13 aacctttttag tcatcatgtt gtaccact                                      28
```

```
<210> SEQ ID NO 14
<211> LENGTH: 30
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 14
tcatcaactt caattttttt taatgtcatt                                    30

<210> SEQ ID NO 15
<211> LENGTH: 18
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 15
attgtcgttt cccgcctt                                                 18

<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 16
tgcttttgga tactaattaa cac                                           23

<210> SEQ ID NO 17
<211> LENGTH: 20
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 17
gcgagctgat ctggacatga                                               20

<210> SEQ ID NO 18
<211> LENGTH: 21
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 18
cacccatccg atgtaggtga c                                             21

<210> SEQ ID NO 19
<211> LENGTH: 15
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 19
ccagcacgtg aataa                                                    15
```

TRANSGENIC BRASSICA EVENT MON 88302 AND METHODS OF USE THEREOF

This application is a divisional of co-pending U.S. patent application Ser. No. 13/151,082, filed Jun. 1, 2011, which claims the benefit of U.S. Provisional Application No. 61/351,317, filed on Jun. 4, 2010, the entire disclosure of which is incorporated herein by reference.

INCORPORATION OF SEQUENCE LISTING

The sequence listing that is contained in the file named "38-21_56992_seqlisting_ST25.txt", which is 20.7 kilobytes (size as measured in Microsoft Windows®) and was created on Jun. 2, 2010, is filed herewith by electronic submission and is incorporated by reference herein.

FIELD OF THE INVENTION

The invention relates to the fields of biotechnology and agriculture and more specifically to the field of transgenic crop plants.

BACKGROUND OF THE INVENTION

Brassica crops are important in many areas of the world. The methods of biotechnology may be applied to these crops to produce crops with improved traits such as herbicide tolerance. Herbicide tolerance may be achieved in transgenic plants by the expression of a transgene capable of providing such tolerance. The expression of a transgene in a plant may be influenced by a combination of factors such as the regulatory elements used in the transgene cassette, the chromosomal location of the transgene insert, and the proximity of any endogenous regulatory elements close to the integration site. For example, it has been observed that there may be wide variation in the overall level of transgene expression or in the spatial or temporal pattern of transgene expression between similarly-produced events. For this reason, it may be necessary to produce and test hundreds of individual plant transformation events in order to ultimately identify one event useful for commercial agricultural purposes. Such an event, once identified as having the desired transgene expression and molecular characteristics, may then be used for introgressing the trait into other genetic backgrounds using plant breeding methods. The resulting progeny would contain the transgenic event and would therefore have the transgene expression characteristics for that trait of the original transformant. This may be used to produce a number of different crop varieties that comprise the improved trait and are suitably adapted to specific local growing conditions.

SUMMARY OF THE INVENTION

The invention provides transgenic plants and seeds comprising event MON 88302, a representative seed sample of which has been deposited with American Type Culture Collection (ATCC) with Accession No. PTA-10955. Plants comprising the event exhibit commercially acceptable tolerance to applications of glyphosate herbicide. The invention provides progeny plants, plant parts, and cells comprising the event; recombinant DNA molecules related to the event and methods of using these molecules; commodity products derived from or comprising the event; and methods of using the event.

The invention provides a plant, seed, cell, progeny plant, or plant part comprising the event and commodity products derived from a plant, cell, plant part, or seed comprising the event. The invention thus provides a plant, seed, cell, progeny plant, plant part, or commodity product comprising a DNA molecule having a nucleotide sequence selected from the group consisting of SEQ ID NO: 1, SEQ ID NO: 2, SEQ ID NO: 3, SEQ ID NO: 4, SEQ ID NO: 6, SEQ ID NO: 7, and SEQ ID NO: 8, and fragments thereof. The invention provides a plant, seed, cell, progeny plant, or plant part comprising a recombinant DNA molecule that produces an amplicon comprising a DNA molecule of the invention, for instance in a DNA amplification method.

The invention provides DNA molecules related to the event. These DNA molecules may comprise nucleotide sequences representing or derived from the junction of the transgene insertion and flanking genomic DNA of event MON 88302, and/or a region of the genomic DNA flanking the inserted DNA, and/or a region of the integrated transgenic DNA flanking the insertion site, and/or a region of the integrated transgenic expression cassette, and/or a contiguous sequence of any of these regions. The invention also provides DNA molecules useful as primers and probes diagnostic for the event. Plants, cells, plant parts, commodity products, progeny, and seeds comprising these molecules are provided.

The invention provides methods, compositions, and kits useful for detecting the presence of DNA derived from the event. The invention provides a method for detection of the event by contacting a sample comprising DNA with a primer set that when used in a nucleic acid amplification reaction with genomic DNA from the event produces an amplicon diagnostic for the event, performing a nucleic acid amplification reaction thereby producing the amplicon, and detecting the amplicon. The invention also provides a method for detection of the event by contacting a sample comprising DNA with a probe that when used in a hybridization reaction with genomic DNA from the event hybridizes to a DNA molecule specific for the event, performing a hybridization reaction, and detecting the hybridization of the probe to the DNA molecule. Kits comprising the methods and compositions of the invention useful for detecting the presence of DNA derived from the event are also provided.

The invention provides a method for controlling weeds in a field by planting plants comprising the event (i.e., planting seeds comprising the events) and then applying an effective dose of glyphosate capable of controlling the weeds without injuring the plants comprising the event.

The invention provides methods of producing a plant and/or seed that tolerates application of glyphosate herbicide by crossing a glyphosate tolerant plant comprising the event or comprising a sequence selected from the group consisting of SEQ ID NO: 1, SEQ ID NO: 2, SEQ ID NO: 3, SEQ ID NO: 4, SEQ ID NO: 6, SEQ ID NO: 7, and SEQ ID NO: 8 with a second plant, thereby producing seed, growing the seed to produce progeny plants, treating the progeny plants with glyphosate, and selecting a progeny plant that comprises the event and is tolerant to glyphosate. The invention provides methods of producing a plant and/or seed that tolerates application of glyphosate herbicide by selfing a glyphosate tolerant plant comprising the event or comprising a sequence selected from the group consisting of SEQ ID NO: 1, SEQ ID NO: 2, SEQ ID NO: 3, SEQ ID NO: 4, SEQ ID NO: 6, SEQ ID NO: 7, and SEQ ID NO: 8, thereby producing seed, growing the seed to produce progeny plants, treating the progeny plants with glyphosate; and selecting a progeny plant that comprises the event and is tolerant to glyphosate.

The invention provides methods of determining the zygosity of a plant or seed comprising the event, by contacting a sample comprising DNA with a first primer set that when used in a nucleic acid amplification reaction with genomic DNA from event MON 88302 produces an amplicon diagnostic for the event, performing a nucleic acid amplification reaction thereby producing the amplicon, detecting the amplicon, contacting the sample with a second primer set that when used in a nucleic-acid amplification reaction with genomic DNA from plants produces a second amplicon comprising the native genomic DNA homologous to the genomic region of a transgene insertion identified as event MON 88302, performing a nucleic acid amplification reaction thereby producing the second amplicon, detecting the second amplicon, and comparing the first and second amplicons in a sample, wherein the presence of both amplicons indicates the sample and thus the plant or seed is heterozygous for the transgene insertion.

The foregoing and other aspects of the invention will become more apparent from the following detailed description.

BRIEF DESCRIPTION OF THE SEQUENCES

Figure 1:
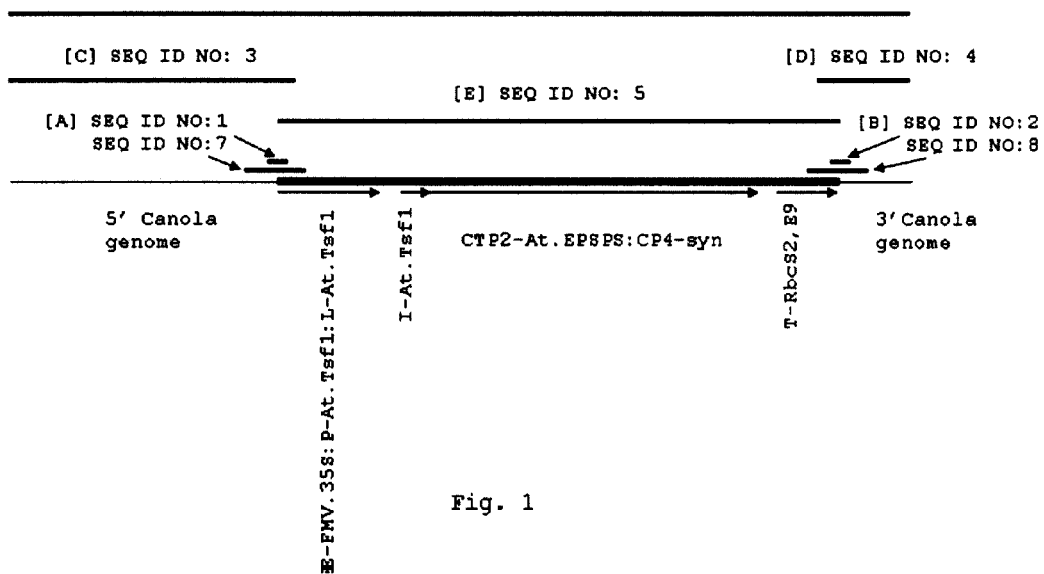
FIG. 1: Diagrammatical representation of event MON 88302; [A] corresponds to the relative position of the 5' junction region; [B] corresponds to the relative position of the 3' junction region; [C] corresponds to the relative position of the flanking region and a portion of the 5' end of the inserted transgenic DNA; [D] corresponds to the relative position of the 3' flanking region and a portion of the 3' end of the inserted transgenic DNA; [E] represents the transgene expression cassette; and [F] represents the contiguous sequence of the *Brassica napus* genomic flanking sequences and transgene expression cassette.

SEQ ID NO: 1—A sixty nucleotide sequence representing the 5' junction sequence between the *Brassica napus* genomic DNA and the integrated transgenic expression cassette. This nucleotide sequence corresponds to positions 762 through 821 of SEQ ID NO: 3 ([C], see FIG. 1) and to positions 762 through 821 of SEQ ID NO: 6.

SEQ ID NO: 2—A sixty nucleotide sequence representing the 3' junction between the integrated expression cassette and the *Brassica napus* genomic DNA. This nucleotide sequence corresponds to positions 313 through 372 of SEQ ID NO: 4 ([D], see FIG. 1), and to positions 5189 through 5248 of SEQ ID NO: 6.

SEQ ID NO: 3—The 5' sequence flanking the inserted DNA of event MON 88302 up to and including a region of transgenic DNA. Nucleotide positions 762 through 821 of SEQ ID NO: 3 correspond to nucleotide positions 1 through 60 of SEQ ID NO: 1; nucleotide positions 742 through 841 of SEQ ID NO: 3 correspond to nucleotide positions 1 through 100 of SEQ ID NO: 7 and nucleotide positions 792 through 956 of SEQ ID NO: 3 correspond to nucleotide positions 1 through 165 of SEQ ID NO: 5.

SEQ ID NO: 4—The 3' sequence flanking the inserted DNA of event MON 88302 up to and including a region of transgenic DNA. Nucleotide positions 313 through 372 of SEQ ID NO: 4 correspond to nucleotide positions 1 through 60 of SEQ ID NO: 2; nucleotide positions 293 through 392 of SEQ ID NO: 4 correspond to nucleotide positions 1 through 100 of SEQ ID NO: 8 and the nucleotide positions 1 through 342 of SEQ ID NO: 4 correspond to nucleotide positions 4086 through 4427 of SEQ ID NO: 5.

SEQ ID NO: 5—The sequence of the integrated transgenic expression cassette conferring glyphosate herbicide tolerance. SEQ ID NO: 5 corresponds to nucleotide positions 792 through 5218 of SEQ ID NO: 6.

SEQ ID NO: 6—A nucleotide sequence representing the contig of the 5' sequence flanking the inserted DNA of event MON 88302 (SEQ ID NO: 3), the sequence of the integrated expression cassette (SEQ ID NO: 5), and the 3' sequence flanking the inserted DNA of event MON 88302 (SEQ ID NO: 4).

SEQ ID NO: 7—A 100-nucleotide sequence representing the 5' junction sequence between the *Brassica napus* genomic DNA and the integrated transgenic expression cassette. This nucleotide sequence corresponds to positions 742 through 841 of SEQ ID NO: 3 ([C], see FIG. 1) and to position 742 through 841 of SEQ ID NO: 6.

SEQ ID NO: 8—A 100-nucleotide sequence representing the 3' junction between the integrated expression cassette and the *Brassica napus* genomic DNA. This nucleotide sequence corresponds to positions 293 through 392 of SEQ ID NO: 4 ([D], see FIG. 1), and to positions 5169 through 5268 of SEQ ID NO: 6.

SEQ ID NO: 9—Primer SQ20901 used to identify event MON 88302. Primer SQ20901 is complementary to the inserted expression cassette at the region close to the 3' transgene insertion border. An amplicon produced using the combination of primers SQ20901 and SQ23770 (SEQ ID NO: 10) is a positive result for the presence of the event MON 88302.

SEQ ID NO: 10 is the sequence of a primer referred to as Primer SQ23770 and used to identify event MON 88302. Primer SQ23770 is complimentary to a 3' region flanking the inserted expression cassette and close to the transgene DNA insertion border. An amplicon produced using the combination of primers SQ20901 (SEQ ID NO: 9) and SQ23770 is a positive result for the presence of the event MON 88302.

SEQ ID NO: 11 is the sequence of a probe referred to as Probe PB 10164 and used to identify event MON 88302. It is complimentary to a 3' region flanking the inserted expression cassette and close to the transgene DNA insertion border. This probe is a 6FAM™-labeled synthetic oligonucleotide. Release of a fluorescent signal in an amplification reaction using primers SQ20901 and SQ23770 (SEQ ID NOs: 9-10) in combination with 6FAM™-labeled probe PB10164 is diagnostic of event MON 88302 in a TAQMAN® assay.

SEQ ID NO: 12 is the sequence of a primer referred to as Primer SQ21948 and used to identify MON 88302 event zygosity.

SEQ ID NO: 13 is the sequence of a primer referred to as Primer SQ24635 and used to identify *Brassica napus* wild-type zygosity.

SEQ ID NO: 14 is the sequence of a primer referred to as Primer SQ22176 and used to identify MON 88302 event and *Brassica napus* wild-type zygosity.

SEQ ID NO: 15 is the sequence of a probe (PB4213) for a MON 88302 event zygosity assay.

SEQ ID NO: 16 is the sequence of a probe (PB10787) for a *Brassica napus* wild-type zygosity assay.

SEQ ID NO: 17 is the sequence of a primer referred to as Primer SQ2563 and used as an internal control in the TAQMAN® assays.

SEQ ID NO: 18 is the sequence of a primer referred to as Primer SQ2564 and used as an internal control in the TAQMAN® assays.

SEQ ID NO: 19 is the sequence of a VIC™-labeled synthetic oligonucleotide probe (PB0751) used as an internal control in the TAQMAN® assays.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "comprising" means "including but not limited to".

The present invention provides transgenic event MON 88302. The term "event" as used herein refers to DNA molecules produced as a result of inserting transgenic DNA into a plant's genome at a particular location on a chromosome. Event MON 88302 refers to the DNA molecules produced as a result of the insertion of transgenic DNA having a sequence provided herein as SEQ ID NO: 5 into a particular location in the *Brassica napus* A genome on linkage group N4. Plants and seeds comprising event MON 88302 are also provided in the present invention. A seed sample containing MON 88302 has been deposited with American Type Culture Collection (ATCC) with Accession No. PTA-10955. Plants comprising MON 88302 exhibit commercially acceptable tolerance to applications of glyphosate herbicide.

A plant comprising the event can refer to the original transformant that includes the transgene inserted into the particular location in the plant's genome. A plant comprising the event can also refer to progeny of the original transformant that include the transgene inserted into the particular location in the plant's genome. Such progeny may be produced by selfing or by a sexual outcross between the transformant, or its progeny, and another plant. Such other plant may be a transgenic plant comprising the same or different transgene and/or a nontransgenic plant, such as one from a different variety. Even after repeated back-crossing to a recurrent parent, the inserted DNA and flanking DNA from the transformed parent is present in the progeny of the cross at the same genomic location.

Transgenic event MON 88302 was created by the insertion of transgenic DNA (provided herein as SEQ ID NO: 5) into linkage group N4 of the A genome of a *Brassica napus* plant. *Brassica napus* is commonly known as rapeseed and specific cultivars may be referred to as canola. As used herein, the term "canola" or "canola plant" refers to a *Brassica* plant capable of being used to produce canola oil (i.e. oil meeting a specific quality designation of containing less than 2% erucic acid) and includes varieties of *Brassica napus, Brassica napobrassica, Brassica rapa, Brassica juncea*, and *Brassica campestris*. Because *Brassica napus* is an allotetraploid arising from the cross and retention of both genomes of *Brassica rapa* (previously *Brassica campestris*) and *Brassica oleracea*, a *Brassica napus* plant comprising transgenic event MON 88302 may be used with breeding methods to introduce the MON 88302 event, and thus the glyphosate tolerance trait, into other members of the *Brassica* genus. Examples of members of the *Brassica* genus useful in practicing the methods of the invention include but are not limited to *Brassica juncea, Brassica napobrassica, Brassica oleracea, Brassica carinata, Brassica napus, Brassica rapa*, and *Brassica campestris*, as well as any other plants belonging to the genus *Brassica* that permit breeding between *Brassica* species.

A DNA molecule comprising event MON 88302 refers to a DNA molecule comprising at least a portion of the inserted transgenic DNA (provided as SEQ ID NO: 5) and at least a portion of the flanking genomic DNA immediately adjacent to the inserted DNA. As such, a DNA molecule comprising event MON 88302 has a nucleotide sequence representing at least a portion of the transgenic DNA insert and at least a portion of the particular region of the genome of the plant into which the transgenic DNA was inserted. The arrangement of the inserted DNA in event MON 88302 in relation to the surrounding plant genome is specific and unique to event MON 88302 and as such the nucleotide sequence of such a DNA molecule is descriptive and identifying for event MON 88302. Examples of the sequence of such a DNA molecule are provided herein as SEQ ID NO: 1, SEQ ID NO: 2, SEQ ID NO: 3, SEQ ID NO: 4, SEQ ID NO: 6, SEQ ID NO: 7, and SEQ ID NO: 8. This DNA molecule is also an integral part of the chromosome of a plant that comprises event MON 88302 and may be passed on to progeny of the plant.

Event MON 88302 confers tolerance to glyphosate herbicide applied to the plant. "Glyphosate" refers to N-phosphonomethyl-glycine and its salts. Glyphosate is an herbicide that has activity on a broad spectrum of plant species. When applied to a plant surface, glyphosate moves systemically through the plant. Glyphosate is phototoxic due to its inhibition of the shikimic acid pathway, which provides a precursor for the synthesis of aromatic amino acids.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the *Brassica napus* genome, which may ultimately result in the expression of a recombinant RNA and/or protein molecule in that organism. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a plant described herein as comprising event MON 88302.

As used herein, the term "transgene" refers to a polynucleotide molecule artificially incorporated into a host cell's genome. Such transgene may be heterologous to the host cell. The term "transgenic plant" refers to a plant comprising such a transgene.

As used herein, the term "heterologous" refers to a first molecule not normally found in combination with a second molecule in nature. For example, a molecule may be derived from a first species and inserted into the genome of a second species. The molecule would thus be heterologous to the host and artificially incorporated into a host cell's genome.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature.

The present invention provides DNA molecules and their corresponding nucleotide sequences. As used herein, the terms "DNA sequence", "nucleotide sequence" and "polynucleotide sequence" refer to the sequence of nucleotides of a DNA molecule, usually presented from the 5' (upstream) end to the 3' (downstream) end. The nomenclature used herein is that required by Title 37 of the United States Code of Federal Regulations §1.822 and set forth in the tables in WIPO Standard ST.25 (1998), Appendix 2, Tables 1 and 3. The present invention is disclosed with reference to only one strand of the two nucleotide sequence strands that are provided in transgenic event MON 88302. Therefore, by implication and derivation, the complementary sequences, also referred to in the art as the complete complement or the reverse complementary sequences, are within the scope of the present invention and are therefore also intended to be within the scope of the subject matter claimed.

The nucleotide sequence corresponding to the complete nucleotide sequence of the inserted transgenic DNA and substantial segments of the *Brassica napus* genomic DNA flanking either end of the inserted transgenic DNA is provided herein as SEQ ID NO: 6. A subsection of this is the inserted transgenic DNA provided as SEQ ID NO: 5. The nucleotide sequence of the genomic DNA flanking the 5' end of the inserted transgenic DNA and a portion of the 5' end of the inserted DNA is provided herein as SEQ ID NO: 3. The nucleotide sequence of the genomic DNA flanking the 3' end of the inserted transgenic DNA and a portion of the 3' end of the inserted DNA is provided herein as SEQ ID NO: 4. The region spanning the location where the transgenic DNA connects to and is linked to the genomic DNA, is referred to herein as the junction. A "junction sequence" or "junction region" refers to a DNA sequence and/or corresponding DNA molecule that spans the inserted transgenic DNA and the adjacent flanking genomic DNA. Examples of a junction sequence of event MON 88302 are provided herein as SEQ ID NO: 1, SEQ ID NO: 2, SEQ ID NO: 7, and SEQ ID NO: 8. The identification of one of these junction sequences in a nucleotide molecule derived from a *Brassica* plant or seed is conclusive that the DNA was obtained from event MON 88302 and is diagnostic for the presence in a sample of DNA from event MON 88302. SEQ ID NO: 1 is a 60 nucleotide sequence spanning the junction between the genomic DNA and the 5' end of the inserted DNA. SEQ ID NO: 7 is a 100 nucleotide sequence spanning the junction between the genomic DNA and the 5' end of the inserted DNA. SEQ ID NO: 2 is a 60 nucleotide sequence spanning the junction between the genomic DNA and the 3' end of the inserted DNA. SEQ ID NO: 8 is a 100 nucleotide sequence spanning the junction between the genomic DNA and the 3' end of the inserted DNA. Any segment of DNA derived from transgenic event MON 88302 that includes SEQ ID NO: 1 or SEQ ID NO: 7 is within the scope of the present invention. Any segment of DNA derived from transgenic event MON 88302 that includes SEQ ID NO: 2 or SEQ ID NO: 8 is within the scope of the present invention. In addition, any polynucleotide comprising a sequence complementary to any of the sequences described within this paragraph is within the scope of the present invention. FIG. 1 illustrates the physical arrangement of SEQ ID NOs: 1-5 and SEQ ID NOs: 7-8 relative to SEQ ID NO: 6 arranged from 5' to 3'. The present invention also provides a nucleic acid molecule comprising a DNA molecule having a sequence that is at least 95%, 96%, 97%, 98%, or 99% identical to the full-length of SEQ ID NO: 6.

The present invention provides exemplary DNA molecules that can be used either as primers or probes for diagnosing the presence of DNA derived from event MON 88302 in a sample. Such primers or probes are specific for a target nucleic acid sequence and as such are useful for the identification of event MON 88302 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of *Brassica napus* genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques, i.e. the product of an amplification reaction. In one embodiment of the invention, an amplicon diagnostic for event MON 88302 comprises a sequence not naturally found in the *Brassica napus* genome. An amplicon of the present invention comprises at least about 40 contiguous nucleotides of SEQ ID NO: 1 or SEQ ID NO: 2, and complements thereof. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening polynucleotide molecule) using as a template the target DNA strand. Primer pairs, as used in the present invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NOs: 9-10. The primer pair provided as SEQ ID NO: 9 and SEQ ID NO: 10 may be used as a first DNA molecule and a second DNA molecule that is different from the first DNA molecule, and both molecules are each of sufficient length of contiguous nucleotides of either SEQ ID NO: 4, SEQ ID NO: 5, or SEQ ID NO: 6 or the complements thereof to function as DNA primers so that, when used together in a thermal amplification reaction with template DNA derived from event MON 88302, an amplicon that is specific and unique to the 3' portion of transgenic event MON 88302 would be produced. This exemplary primer pair may be used to amplify a 3' junction region diagnostic for event MON 88302. Similarly, the invention provides primer pairs that may be used to amplify a 5' junction region diagnostic for event MON 88302. Such primers may comprise a first DNA molecule and a second DNA molecule that is different from the first DNA molecule, both of sufficient length of contiguous nucleotides of SEQ ID NO: 3, SEQ ID NO: 5, or SEQ ID NO: 6 or the complements thereof to function as DNA primers so that, when used together in a thermal amplification reaction with template DNA derived from event MON 88302, an amplicon that is specific and unique to the 5' portion of transgenic event MON 88302 would be produced.

A "probe" is an isolated nucleic acid that is complementary to a strand of a target nucleic acid. Probes according to the present invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. In one embodiment of the invention, a probe diagnostic for event MON 88302 comprises a sequence not naturally found in the *Brassica napus* genome. An exemplary DNA molecule useful as a probe is provided as SEQ ID NO: 11.

Probes and primers according to the present invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from event MON 88302 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985). As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

As used herein, the term "isolated" refers to at least partially separating a molecule from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or a fragment thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying event MON 88302, selecting plant varieties or hybrids comprising event MON 88302, detecting the presence of DNA derived from event MON 88302 in a sample, and monitoring samples for the presence and/or absence of event MON 88302 or plants and plant parts comprising event MON 88302.

The present invention provides plants, progeny, seeds, plant cells, plant parts (such as pollen, ovule, pod, flower, root or stem tissue, fibers, and leaves), and commodity products. These plants, progeny, seeds, plant cells, plant parts, and commodity products contain a detectable amount of a polynucleotide of the present invention, i.e., such as a polynucleotide having at least one of the sequences provided as SEQ ID NO: 1, SEQ ID NO: 2, SEQ ID NO: 7, or SEQ ID NO: 8. Plants, progeny, seeds, plant cells, and plant parts of the present invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, disease resistance, improved nutritional quality, and/ or increased herbicide tolerance, in which the desirable trait is measured with respect to a comparable plant lacking such additional transgene.

The present invention provides plants, progeny, seeds, plant cells, and plant part such as pollen, ovule, pod, flower, root or stem tissue, and leaves derived from a transgenic plant comprising event MON 88302. A representative sample of seed comprising event MON 88302 has been deposited according to the Budapest Treaty for the purpose of enabling the present invention. The repository selected for receiving the deposit is the American Type Culture Collection (ATCC) having an address at 10801 University Boulevard, Manassas, Va. USA, Zip Code 20110. The ATCC repository has assigned the accession No. PTA-10955 to the event MON 88302 seed.

The present invention provides a microorganism comprising a DNA molecule having SEQ ID NO: 1, SEQ ID NO: 2, SEQ ID NO: 7, or SEQ ID NO: 8 present in its genome. An example of such a microorganism is a transgenic plant cell. Microorganisms, such as a plant cell of the present invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the present invention is a method of using a microorganism of the present invention. Methods of using microorganisms of the present invention, such as transgenic plant cells, include (i) methods of producing transgenic cells by integrating recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

As used herein, "progeny" includes any plant, seed, plant cell, and/or regenerable plant part comprising the event DNA derived from an ancestor plant and/or a polynucleotide having at least one of the sequences provided as SEQ ID NO: 1, SEQ ID NO: 2, SEQ ID NO: 7, or SEQ ID NO: 8. Plants, progeny, and seeds may be homozygous or heterozygous for the transgene. Progeny may be grown from seeds produced by a plant comprising event MON 88302 and/or from seeds produced by a plant fertilized with pollen from a plant comprising event MON 88302.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another plant, to produce a varietal or a hybrid seed or plant. The other plant may be transgenic or non-transgenic. A varietal or hybrid seed or plant of the present invention may thus be derived by crossing a first parent that lacks the specific and unique DNA of the event MON 88302 with a second parent comprising event MON 88302, resulting in a hybrid comprising the specific and unique DNA of the event MON 88302. Each parent can be a hybrid or an inbred/varietal, so long as the cross or breeding results in a plant or seed of the present invention, i.e., a seed having at least one allele containing the specific and unique DNA of event MON 88302 and/or SEQ ID NO: 1 and SEQ ID NO: 2. Two different transgenic plants may thus be mated to produce hybrid offspring that contain two independently segregating, added, exogenous genes. For example, the glyphosate tolerant plant comprising event MON 88302 can be crossed with another transgenic plant to produce a plant having the characteristics of both transgenic parents. One example of this would be a cross of glyphosate tolerant *Brassica* plant comprising event MON 88302 with a *Brassica* plant such as mustard or canola and having one or more additional traits, resulting in a progeny plant or seed that is tolerant to glyphosate and has one or more additional traits. *Brassica* plants having desirable transgenic traits are known in the art, including but not limited to *Brassica* plants having the trait of herbicide tolerance (e.g., event RT200, event RT73, event MS1, event RF1, event RF2, Topas 19/2, MS8, RF3, T45), a hybrid breeding system or a fertility system (e.g., event MS1, event MS8, event RF1, event RF2, event Rf3), insect control, enhanced yield, disease resistance (e.g., Sclerotinia Resistance, Blackleg Resistance, Clubroot Resistance, Fusarium Wilt Resistance), altered or enhanced oil composition (e.g., event pCGN3828-212/86-18, event pCGN3828-212/23), all described for example in the publicly available United States Department of Agriculture (USDA) Animal and Plant Health Inspection Service (APHIS) listing of Petitions for Nonregulated Status. *Brassica* plants having desirable non-transgenic traits are known in the art, including but not limited to traits for herbicide tolerance (e.g., 1471 for imidazolinone tolerance, CLB-1 for imidazolinone tolerance, TTC for triazine tolerance), pathogen resistance, insect control, enhanced yield, disease resistance (e.g., Sclerotinia Resistance, Blackleg Resistance, Clubroot Resistance, Fusarium Wilt Resistance), altered or enhanced oil composition (including low linolenic and/or high oleic), altered chemical and/or nutritional composition, altered protein composition, cold tolerance, drought tolerance, altered maturity and/or flowering, and other altered or improved agronomic qualities.

Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The present invention provides a plant part that is derived from plants comprising event MON 88302. As used herein, a "plant part" refers to any part of a plant which is comprised of material derived from a plant comprising event MON 88302. Plant parts include but are not limited to pollen, ovule, pod, flower, root or stem tissue, fibers, and leaves. Plant parts may be viable, nonviable, regenerable, and/or non-regenerable.

The present invention provides a commodity product that is derived from a plant comprising event MON 88302. As used herein, a "commodity product" refers to any composition or product which is comprised of material derived from a plant, seed, plant cell, or plant part comprising event MON 88302. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, and any other food for human consumption; and biomasses and fuel products. Viable commodity products include but are not limited to seeds and plant cells. A plant comprising event MON 88302 can thus be used to manufacture any commodity product typically acquired from a *Brassica* plant. Any such commodity product that is derived from the plants comprising event MON 88302 may contain at least a detectable amount of the specific and unique DNA corresponding to event MON 88302, and specifically may contain a detectable amount of a polynucleotide containing at least 40 contiguous nucleotides of SEQ ID NO: 1 or SEQ ID NO: 2. Any standard method of detection for polynucleotide molecules may be used, including methods of detection disclosed herein. A commodity product is within the scope of the present invention if there is any detectable amount of SEQ ID NO: 1 or SEQ ID NO: 2 in the commodity product.

The plants, progeny, seeds, plant cells, plant parts (such as pollen, ovule, pod, flower, root or stem tissue, and leaves), and commodity products of the present invention are therefore useful for, among other things, growing plants for the purpose of producing seed and/or plant parts comprising event MON 88302 for agricultural purposes, producing progeny comprising event MON 88302 for plant breeding and research purposes, use with microbiological techniques for industrial and research applications, and sale to consumers.

The present invention provides methods for controlling weeds in a field. A method for controlling weeds in a field is provided that consists of planting plants comprising event MON 88302 in a field and applying at least one herbicidally effective dose of glyphosate to the field for the purpose of controlling weeds in the field without injuring plants comprising MON 88302. Another method for controlling weeds in a field is also provided that consists of applying at least one herbicidally effective dose of glyphosate to the field to control weeds in the field and then planting crops comprising event MON 88302 in the field. The methods of the invention may be used alone or in combination. Application of glyphosate may be pre-plant (i.e., anytime prior to planting seed comprising event MON 88302 including, but not limited to, about 14 days pre-planting to about 1 day pre-planting or concurrent with sowing seed comprising event MON 88302), pre-emergence (i.e., any time after seed comprising event MON 88302 is planted and before plants comprising event MON 88302 emerge), and/or post-emergence (i.e., any time after plants comprising event MON 88302 emerge). In practicing the methods of the invention, multiple applications of glyphosate may be used over a growing season, for example, as two applications (such as a pre-planting application and a post-emergence application or a pre-emergence application and a post-emergence application) or three applications (such as a pre-planting application, a pre-emergence application, and a post-emergence application). The total glyphosate applied over the growing season may thus include one or more in-season application where the sum of multiple in-season applications adds together to make the total glyphosate applied. As used herein, an amount of glyphosate effective to control the growth of weeds, i.e., an herbicidally effective dose of glyphosate for use in the field as an in-crop application to control the growth of weeds in the filed, should consist of a range from about 0.125 pounds of glyphosate per acre to about 6.4 pounds of glyphosate per acre total over a growing season. For example, an herbicidally effective dose of glyphosate for use in the field as an in-crop application may be at least about 0.125, about 0.5, about 1.0, about 1.6, about 2.0, about 2.5, about 3.0, about 3.5, about 4.0, about 4.5, about 5.0, about 5.5, about 6.0, or about 6.4 pounds per acre total over a growing season.

Methods for producing an herbicide tolerant plant comprising transgenic event MON 88302 are provided. Transgenic plants used in these methods may be homozygous or heterozygous for the transgene. Progeny plants produced by these methods may be varietal or hybrid plants; may be grown from seeds produced by a plant and/or from seed comprising event MON 88302 produced by a plant fertilized with pollen from a plant comprising event MON 88302; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

A plant that tolerates application of glyphosate herbicide may be produced by sexually crossing a plant comprising event MON 88302 comprising a polynucleotide molecule comprising the sequence of SEQ ID NO: 1 and SEQ ID NO: 2 with another plant and thereby producing seed, which is then grown into progeny plants. These progeny plants may then be treated with glyphosate herbicide to select for progeny plants that are tolerant to glyphosate herbicide. Alternatively, these progeny plants may be analyzed using diagnostic methods to select for progeny plants that contain the event MON 88302 DNA. The other plant used in the crossing may or may not be tolerant to glyphosate herbicide and may or may not be transgenic. The progeny plant and/or seed produced may be varietal or hybrid seed. In practicing this method, the step of sexually crossing one plant with another plant, i.e., cross-pollinating, may be accomplished or facilitated by human intervention, for example: by human hands collecting the pollen of one plant and contacting this pollen with the style or stigma of a second plant; by human hands and/or human actions removing, destroying, or covering the stamen or anthers of a plant (e.g., by manual intervention or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma; by selective placement of plants (e.g., intentionally planting plants in pollinating proximity); and/or by application of chemicals to precipitate flowering or to foster receptivity (of the stigma for pollen).

A plant that tolerates application of glyphosate herbicide may be produced by selfing a plant comprising event MON 88302 comprising a polynucleotide molecule comprising the sequence of SEQ ID NO: 1 and SEQ ID NO: 2 and thereby producing seed, which is then grown into progeny plants. These progeny plants may then be treated with glyphosate herbicide to select for progeny plants that are tolerant to glyphosate herbicide. Alternatively, these progeny plants may be analyzed using diagnostic methods to select for progeny plants that contain the event MON 88302 DNA. In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

Progeny plants and seeds encompassed by these methods and produced by using these methods will be distinct from other plants, for example because the progeny plants and seeds: are recombinant and as such created by human intervention; are glyphosate herbicide tolerant; contain at least one allele that consists of the transgene DNA of the present invention; and/or contain a detectable amount of a polynucleotide sequence selected from the group consisting of SEQ ID NO: 1 and SEQ ID NO: 2. A seed may be selected from an individual progeny plant, and so long as the seed comprises SEQ ID NO: 1 and SEQ ID NO: 2, it will be within the scope of the present invention.

In practicing the present invention, two different transgenic plants can be crossed to produce hybrid offspring that contain two independently segregating heterologous genes. Selfing of appropriate progeny can produce plants that are homozygous for both genes. Back-crossing to a parental plant and out-crossing with a non-transgenic plant are also contemplated, as is vegetative propagation. Descriptions of other methods that are commonly used for different traits and crops can be found in one of several references, e.g., Fehr, in Breeding Methods for Cultivar Development, Wilcox J. ed., American Society of Agronomy, Madison Wis. (1987).

The plants and seeds used in the methods disclosed herein may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a plant lacking such additional transgene.

The methods of the present invention are therefore useful for, among other things, controlling weeds in a field while growing plants for the purpose of producing seed and/or plant parts comprising event MON 88302 for agricultural or research purposes, selecting for progeny comprising event MON 88302 for plant breeding or research purposes, and producing progeny plants and seeds comprising event MON 88302.

The plants, progeny, seeds, plant cells, plant parts (such as pollen, ovule, pod, flower, root or stem tissue, and leaves), and commodity products of the present invention may be evaluated for DNA composition, gene expression, and/or protein expression. Such evaluation may be done by using standard methods such as PCR, northern blotting, southern analysis, western blotting, immuno-precipitation, and ELISA or by using the methods of detection and/or the detection kits provided herein.

Methods of detecting the presence of materials specific to event MON 88302 in a sample are provided. One method consists of detecting the presence of DNA specific to and derived from a cell, tissue, or plant comprising event MON 88302. The method provides for a template DNA sample to be contacted with a primer pair that is capable of producing an amplicon from event MON 88302 DNA upon being subjected to conditions appropriate for thermal amplification, particularly an amplicon that contains at least 40 contiguous nucleotides of either SEQ ID NO: 1 or SEQ ID NO: 2 or the complements thereof. The amplicon is produced from a template DNA molecule derived from event MON 88302, so long as the template DNA molecule incorporates the specific and unique nucleotide sequences as set forth in SEQ ID NO: 1 and SEQ ID NO: 2. The amplicon may be single or double stranded DNA or RNA, depending on the polymerase selected for use in the production of the amplicon. The method provides for detecting the amplicon molecule produced in any such thermal amplification reaction, and confirming within the sequence of the amplicon the presence of the nucleotides corresponding to SEQ ID NO: 1 or SEQ ID NO: 2 or the complements thereof. The detection of the nucleotides corresponding to SEQ ID NO: 1 or SEQ ID NO: 2 or the complements thereof in the amplicon are determinative and/or diagnostic for the presence of event MON 88302 specific DNA and thus biological material comprising event MON 88302 in the sample.

Another method is provided for detecting the presence of a DNA molecule corresponding to SEQ ID NO: 3 and SEQ ID NO: 4 in a sample consisting of material derived from plant or plant tissue. The method consists of (i) extracting a DNA sample from a plant, or from a group of different plants, (ii) contacting the DNA sample with a DNA probe molecule that exhibits at least 40 contiguous nucleotides as set forth in either SEQ ID NO: 1 or SEQ ID NO: 2, (iii) allowing the probe and the DNA sample to hybridize under stringent hybridization conditions, and then (iv) detecting a hybridization event between the probe and the target DNA sample. Detection of the hybrid composition is diagnostic for the presence of SEQ ID NO: 3 or SEQ ID NO: 4, as the case may be, in the DNA sample. Absence of hybridization is alternatively diagnostic of the absence of the transgenic event in the sample. Alternatively, determining that a particular plant contains either or both of the sequences corresponding to SEQ ID NO: 1 or SEQ ID NO: 2, or the complements thereof, is determinative that the plant contains at least one allele corresponding to the event MON 88302.

It is thus possible to detect the presence of a nucleic acid molecule of the present invention by any well known nucleic acid detection method such as the polymerase chain reaction (PCR) or DNA hybridization using nucleic acid probes. An event-specific PCR assay is discussed, for example, by Taverniers et al. (J. Agric. Food Chem., 53: 3041-3052, 2005) in which an event-specific tracing system for transgenic maize lines BO 1, Bt176, and GA21 and for transgenic event RT73 is demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

DNA detection kits are provided. One type of kit contains at least one DNA molecule of sufficient length of contiguous nucleotides of SEQ ID NO: 3, SEQ ID NO: 5, or SEQ ID NO: 6 to function as a DNA primer or probe specific for detecting the presence of DNA derived from transgenic event MON 88302 in a sample. The DNA molecule being detected with the kit contains at least 40 contiguous nucleotides of the sequence as set forth in SEQ ID NO: 1. Alternatively, the kit may contain at least one DNA molecule of sufficient length of contiguous nucleotides of SEQ ID NO: 4, SEQ ID NO: 5, or SEQ ID NO: 6 to function as a DNA primer or probe specific for detecting the presence of DNA derived from transgenic event MON 88302 in a sample. The DNA molecule being detected with the kit contains at least 40 contiguous nucleotides as set forth in SEQ ID NO: 2.

An alternative kit employs a method in which the target DNA sample is contacted with a primer pair as described above, then performing a nucleic acid amplification reaction sufficient to produce an amplicon comprising at least 40 contiguous nucleotides of SEQ ID NO: 1 or SEQ ID NO: 2. Detection of the amplicon and determining the presence of no fewer than 40 contiguous nucleotides of SEQ ID NO: 1 or SEQ ID NO: 2 or the complements thereof within the sequence of the amplicon is diagnostic for the presence of event MON 88302 specific DNA in a DNA sample.

A DNA molecule sufficient for use as a DNA probe is provided that is useful for determining, detecting, or for diagnosing the presence or even the absence of DNA specific and unique to event MON 88302 DNA in a sample. The DNA molecule contains at least 40 contiguous nucleotides of SEQ ID NO: 1, or the complement thereof, or at least 40 contiguous nucleotides of SEQ ID NO: 2, or the complement thereof.

Nucleic-acid amplification can be accomplished by any of the various nucleic-acid amplification methods known in the art, including thermal amplification methods. The sequence of the heterologous DNA insert, junction sequences, or flanking sequences from event MON 88302 (with representative seed samples comprising event MON 88302 deposited as ATCC PTA-10955) can be verified (and corrected if necessary) by amplifying such sequences from the event using primers derived from the sequences provided herein followed by standard DNA sequencing of the amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following thermal amplification of the region of interest (using one primer in the inserted sequence and one in the adjacent flanking genomic sequence), a single-stranded amplicon can be hybridized to the immobilized oligonucleotide and serve as a template for a single base extension reaction using a DNA polymerase and labelled ddNTPs specific for the expected next base. Readout may be fluorescent or ELISA-based. Detection of a fluorescent or other signal indicates the presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to a single-stranded amplicon from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. ddNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon. Using this method an oligonucleotide is designed which overlaps the genomic flanking and inserted DNA junction. The oligonucleotide is hybridized to single-stranded amplicon from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) may also be used to detect and/or quantifying the presence of a DNA sequence using the instructions provided by the manufacturer. Briefly, a FRET oligonucleotide probe is designed which overlaps the genomic flanking and insert DNA junction. The FRET probe and amplification primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and amplification primers (one primer in the insert DNA sequence and one in the flanking genomic sequence) are cycled in the presence of a thermostable polymerase and dNTPs. Following successful amplification, hybridization of the FRET probe to the target sequence results in the removal of the probe secondary structure and spatial separation of the fluorescent and quenching moieties resulting in the production of a fluorescent signal. The fluorescent signal indicates the presence of the flanking/transgene insert sequence due to successful amplification and hybridization.

Other described methods, such as, microfluidics (US Patent Publication No. 2006068398, U.S. Pat. No. 6,544,734) provide methods and devices to separate and amplify DNA samples. Optical dyes used to detect and measure specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of event MON 88302 in a sample and can be applied to methods for breeding plants containing the appropriate event DNA. The kits may contain DNA primers or probes that are similar or complementary to SEQ ID NO: 1-6, or fragments or complements thereof.

The kits and detection methods of the present invention are therefore useful for, among other things, identifying event MON 88302, selecting plant varieties or hybrids comprising event MON 88302, detecting the presence of DNA derived from the event MON 88302 in a sample, and monitoring samples for the presence and/or absence of event MON 88302 or plants, plant parts or commodity products comprising event MON 88302.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Brassica napus and MON 88302 Event Selection

This example describes how transgenic events were created and how event MON 88302 was selected. The transgenic event MON 88302 was generated by Agrobacterium-mediated transformation of Brassica napus cells with the transgenic DNA illustrated in FIG. 1, the sequence of which is set forth in SEQ ID NO: 5. The transgene insert provided as SEQ ID NO: 5 is an expression cassette comprising a chimeric promoter consisting of: an enhancer molecule derived from 35S enhancer from figwort mosaic virus (E-FMV.35S) operably linked to a promoter molecule derived from derived from Arabidopsis thaliana Tsf1 gene (P-At.Tsf1) operably linked to a leader molecule derived from Arabidopsis thaliana Tsf1 gene (L-At.Tsf1); operably linked to an intron sequence derived from Arabidopsis thaliana Tsf1 gene (I-At.Tsf1); operably linked to a DNA molecule encoding a chloroplast transit peptide (CTP2, Arabidopsis thaliana EPSPS); operably linked to a DNA molecule encoding a glyphosate resistant EPSPS (CP4-syn); operably connected to a 3' UTR DNA molecule derived from Pisum sativum gene (T-RbcS2, E9).

Explants from Brassica napus were first each transformed with one of five expression cassettes using Agrobacterium-mediated transformation. Transformed cells were then selected on media containing glyphosate and surviving cells were regenerated into plants. Over 23,000 explants were generated and from this 224 total individual R0 events were produced and used for subsequent screening (Table 1).

TABLE 1

Transformation of Brassica napus and MON 88302 event selection

| con-struct | transfor-mation | Sin-gle copy | GH effi-cacy | GH molec-ular | FT First year | FT Second year | Lead Events |
|---|---|---|---|---|---|---|---|
| 1 | 97 events from 8325 explants | 37 | 24 | 16 | 16 | 13 advanced 8 tested | 3 |
| 2 | 69 events from 4625 explants | 32 | 5 | 3 | 3 | 0 | — |
| 3 | 43 events from 10245 explants | 11 | 0 | — | — | — | — |
| 4 | ~30 events | 14 | 6 | NA | 3 | 0 | — |
| 5 | ~25 events | 10 | 6 | NA | 3 | 0 | — |

Tissue samples of the events were screened using TAQMAN® PCR analysis to eliminate multi-copy and/or molecularly complex events. From the initial 224 events, 104 were advanced based on the presence of a single copy of the transgene and the absence of vector backbone sequences as determined by TAQMAN® PCR analysis. Specifically, from construct 1 (with the initial 97 events) 37 R1 events were advanced; from construct 2 (with the initial 69 events) 32 R1 events were advanced; from construct 3 (with the initial 43 events) 11 R1 events were advanced; from construct 4 (with approximately 30 events) 14 R1 events were advanced, and from construct 5 (with approximately 25 events) 10 R1 events were advanced.

The 104 events containing a single copy of the transgene were advanced to greenhouse testing (GH), including additional molecular analysis and efficacy testing. R1 greenhouse molecular analysis included: an initial Southern blot analysis to confirm the presence of a single copy of the transgene and the absence of vector backbone sequences; CP4 protein expression levels measured at the 3-4 leaf stage, the rosette stage and in the seed; and CP4 processing as measured by Western blot analysis (events from constructs 4 and 5 were not included in this analysis). R1 greenhouse efficacy testing included: segregation, Chlorosis/Necrosis, vegetative tolerance, first flower, growth reduction, male reproductive tolerance as measured by pollen viability, and seed counts. From analysis of the greenhouse molecular and efficacy testing for the 104 events, 25 events were advanced to first year field trials. Specifically, for construct 1 there were 16 R2 events from the 37 R1 events tested that were advanced; for construct 2 there were 3 R2 events from the 32 R1 events tested that were advanced; for construct 3, with 11 R1 events advanced to greenhouse testing, 0 R2 events were advanced; for construct 4 there were 3 R2 events from the 14 R1 events tested that were advanced; for construct 5 there were 3 R2 events from the 10 R1 events tested that were advanced to field testing.

The 25 R2 events were then analyzed in first year field testing for agronomic evaluation in paired plots at the same locations. Agronomic field trials were initiated to evaluate the impact of gene insertion on plant growth and development. The 16 R2 events from construct 1 were evaluated at 5 locations. The 3 R2 events from construct 2, the 3 R2 events from construct 4, and the 3 R2 events from construct 5 were evaluated at 4 locations. Each study contained the positive and negative isoline pair of each event, as well as the parental transformation germplasm and a commercial variety. For agronomic evaluation, plant vigor, early stand, date of first flower, and plant height were observed to assess plant development. Yield data were also evaluated as an indication of gene insertional effect on plant growth and development. A paired split plot design with 3 replications was used with event as whole plots and isolines as subplots. Positive and negative isolines of each event were paired while a commercial variety and the transformation background were paired and included as controls. Plots were maintained weed-free throughout the season employing conventional herbicide programs supplemented by hand-weeding; as necessary. No glyphosate treatments were applied in this field protocol.

An emergence/stand count for each plot was taken at 7 to 10 days after planting. Cotyledons that had completely cleared the soil were considered "emerged". Plant vigor was determined at the 2 to 3 leaf stage (prior to the first herbicide application of the paired plot of the efficacy testing) using a scale ranging between 1 (excellent vigor), with 5 being average, and 9 (poor vigor). The date of first flower was recorded after all plots had begun flowering and was expressed as percentage of open flowers per plant per plot. Plant height of 5 plants per plot was measured from the soil surface to the top of highest raceme at mid to late flower and expressed in cm. Uniformity and standability were estimated using a scale ranging between 1 (excellent), with 5 being average, and 9 (poor). Each trial was harvested after majority of plots had reached maturity. Some plots were directly combined while other plots were pushed once maturity was reached and the swath was combined approximately 10 days thereafter. Moisture and individual seed weights were recorded (lb/A) and a seed samples were collected for oil and protein analysis. Each location was analyzed individually and averages across locations were analyzed using statistical software. Data were screened for outliers using the standard two-pass procedure based on deleted studentized residuals using a Bonferroni adjustment for an experiment-wise Type I error rate of 5% at each location. Outliers were removed prior to analysis. The standard analysis of variance for a split-plot design was performed with restricted maximum likelihood estimation. Least-squares means were calculated for each isoline of each event, and t-tests with comparison-wise error rates of 5% were used to determine the significance of gene insertion on canola growth characteristics. Event traits of positive isolines were compared to the traits of the corresponding negative isolines. Due to differences in maturity between events, comparison between positive isolines and the pooled negative isolines as well as comparisons to the commercial standard and transformation background were excluded.

Results from first year agronomy field trials indicated that both of the two constructs produced multiple events in which agronomic characteristics and yield were not negatively impacted by gene insertion. Based on agronomic evaluation, 15 events were candidates to be advanced to second year field trials. Specifically, 14 events from construct 1 (16 R2 events in field trials) and 1 event from construct 2 (3 R2 events in field trials) were candidates to be advanced to second year field trials.

The 25 events were also evaluated in first year field testing for efficacy located at the same testing site as the agronomy field trials. Efficacy field trials were initiated to evaluate the vegetative and reproductive tolerance of the events to sequential applications of glyphosate at various application timings and rates. The 16 R2 events from construct 1 were evaluated at 5 locations. The 3 R2 events from construct 2, the 3 R2 events from construct 4, and the 3 R2 events from construct 5 were evaluated at 4 locations. Each study contained the positive isoline of each event and two commercial varieties. A split plot design with 3 replications was used with herbicide treatments as whole plots and event entries as subplots. A non-sprayed treatment was included for comparison.

Events were evaluated for vegetative and reproductive tolerance to either a single application of 1.6 lb AE/A or two sequential applications of 0.8 lb AE/A when applied from crop emergence up to first flower. Roundup WeatherMAX® was applied at three different rates that were equivalent to 2×, 4×, and 8× of the single application rate (Table 2). The initial application was made at the four leaf stage followed by a second application at the prebolt stage. To minimize potential plant damage from surfactants and other formulation components, spray solutions to deliver 3.2 and 6.4 lb AE/A (4× and 8×) were prepared using 1.6 lb AE/A of Roundup WeatherMAX® as base rate and adding technical material (glyphosate without surfactant) to achieve the desired rate. All applications were made using a tractor mounted spray boom equipped with flat-fan nozzles calibrated to deliver 10 to 20 GPA.

Data Collection was performed as above. Glyphosate injury was assessed as follows. Prior to each glyphosate application, plant height and number of leaves for 5 plants per plot in the treated and non-treated plots were documented. To determine if glyphosate caused injury to the events, visual estimates of percent chlorosis and percent necrosis were taken at 7 to 10 days after each glyphosate application. Vegetative injury was rated after the first glyphosate application while reproductive percent chlorosis/necrosis was evaluated after the second application using a scale ranging from 0% (no injury) to 100% (plant death). Growth reduction was evaluated at 14 to 21 days after each application using a scale ranging from 0 to 100%. Vegetative growth reduction was evaluated after the first application while reproductive growth reduction was determined after the sequential application. Least-squares means were calculated for each combination of glyphosate level and event, and t-tests were used to determine the significance of the effects of glyphosate on event tolerance. Event yields from glyphosate treatments were compared to the yield of the non-treated control as well as to the commercial standard, RT73, within each herbicide rate, and comparisons across herbicide rates were made for each event.

Results from the first year efficacy field trials indicate that construct 1 produced events which had excellent vegetative and reproductive tolerance to glyphosate. Vegetative injury observed at the 2× product concept rate was very minor and considered to be commercially insignificant. Outstanding reproductive tolerance for construct 1 events was observed. Yield of all construct 1 events was not negatively impacted by glyphosate, regardless of rate, with the exception of one event which showed a significant yield reduction at the highest application rate (6.4 lb AE/A followed by 6.4 lb AE/A). Events derived from construct 2 did not have sufficient vegetative glyphosate tolerance for advancement. Unacceptable levels of injury were observed at all glyphosate rates tested. Glyphosate significantly reduced the yield of all construct 2 events, regardless of application rate. Events derived from construct 4 and 5 did not perform as well as events from construct 1 and therefore were not advanced to second year field testing. Based on the first year field testing, 13 events from construct 1 were advanced to second year field testing.

Example 2

Comparison of RT73 to MON 88302

Field trials were then designed to evaluate MON 88302 compared to the current commercial Genuity™ Roundup Ready® Canola (RT73 event). Comparisons of MON 88302 to RT73 showed that MON 88302 provided superior crop tolerance to higher glyphosate application rates thus enabling improved weed control at higher glyphosate rates of hard to control weeds such as dandelion, Canada thistle, foxtail barley, wild buckwheat, common-lambsquarter, and kochia. Comparisons of MON 88302 to RT73 also showed that MON 88302 provided superior crop tolerance to a wider application range for glyphosate thus enabling glyphosate application over a wider window ranging from post emergence to first flower, enabling yield-robbing weed control even at a later growth stage of the crop than was possible with RT73. The MON 88302 combination of an increased tolerance to higher glyphosate rates and tolerance to glyphosate applications at a later crop stage provides the advantage, as compared to RT73, of allowing for application of glyphosate at a later growth stage when environmental conditions have limited early applications and/or improved control of late flushes of weeds that would reduce crop yield.

The current registered glyphosate rate for the Genuity™ Roundup Ready® Canola system (event RT73) is a single application of 675 g ae/ha or two 450 g ae/ha applications up to the six leaf stage of the canola crop. RT73 was compared with the MON 88302 event at multiple single application rates of glyphosate. Applications were made from post emergence to the first flower of the canola crop. The Genuity™ Roundup Ready® Canola system (RT73 event) was represented by the commercial open pollinated variety 34-65, and event MON88302 was transformed into the Ebony germplasm.

Eight trials were established with six taken to harvest (one site was lost to drought and one site was lost to hail, and data from one harvested site was not used due to the coefficient of variation (CV) exceeding the predetermined cut-off value). Standard canola growing practices were utilized throughout the season to optimize plant growth. Pre-emergent and post-emergent conventional herbicides and seed treatment containing fungicide and insecticide were used to minimize pest pressure. Trials were set up as a split block design with Genuity™ Roundup Ready® Canola (RT73 event) or MON 88302 systems blocked and herbicide rates randomized within the block. Plots were two by six meters and replicated three times. Plots were sprayed with handheld boom sprayers at 100-110 l/ha application rate at the appropriate crop stage. The Canadian formulation of Roundup WeatherMAX® (540 g/L) was used as the glyphosate product. The four to six leaf stage was defined as four to six true leaves on the main stem, and first flower was when 50% of the plants had at least one flower. Percent chlorosis (% CHLR) was recorded seven to ten days after herbicide application (DAT or days after treatment). Percent chlorosis is a visual estimate of the amount of yellowing on the leaves of plants as a result of herbicide treatment compared to the untreated check on a 1 to 100 scale. Percent growth reduction (% GR) was recorded 14-21 days after herbicide application (DAT). Percent growth reduction is a visual evaluation used to describe plant growth reduction consisting of, but not limited to, reduced height and/or quantity of foliage for the treated area. The evaluation pertains only to the above ground portion of the plant. Percent growth reduction is compared to the non-treated check and is rated on a 1 to 100 scale. Maturity was recorded as days after planting to when 30% of the seeds on the main raceme are brown/black in color. Percent seed moisture was recorded electronically during harvesting. All plots were swathed and then allowed to dry until seed moisture was low enough to facilitate harvesting. Weight and seed moisture was recorded electronically during harvesting and converted to bushels/acre at 10% seed moisture. Each location was analyzed individually and averages across locations were analyzed using statistical software. Data were screened for outliers using the standard two-pass procedure based on deleted studentized residuals using a False Discovery Rate (FDR) adjustment for an experiment-wise Type I error rate of 5% at each location. Outliers were removed prior to analysis. The standard analysis of variance for a split-plot design was performed by mixed model with restricted maximum likelihood estimation-variety and herbicide treatments were treated as fixed effects, replications and locations were random effects. Least-squares means were calculated for each variety and each treatment, and t-tests with comparison-wise error rates of 5% were used to determine the significance between variety and control at each herbicide treatment level on canola growth characteristics. Crop injury, maturity, and yield were measured to assess benefits.

Data on the glyphosate tolerance of canola comprising event RT73 compared to canola comprising event MON 88302 are provided in Table 2. Briefly, the glyphosate tolerance of MON 88302 was superior to the glyphosate tolerance of RT73 in both the tolerance of increased glyphosate application rates (g ae/ha) and the range of crop stage where glyphosate application was tolerated. For example, RT73 showed 4.7% chlorosis at the 1800 g ae/ha application rate to the 4-6 leaf stage, where MON 88302 showed only 1.7% chlorosis at a similar rate at this stage and no increased chlorosis at double the rate (3600 g ae/ha). In addition, MON 88302 event showed no percent growth reduction at the 1800 g ae/ha application rate to the 4-6 leaf stage while RT73 had a 5.3% growth reduction. At the 3600 g ae/ha glyphosate rate at the four to six leaf and first flower crop application stages RT73 showed 10% chlorosis, while MON 88302 showed only 1.7% and 4.7%, respectively. At the 3600 g ae/ha glyphosate rate at the four to six leaf and first flower crop application stages RT73 showed 20.8% and 8.1% growth reduction, respectively, while MON 88302 showed only 0.3% and 1.1%, respectively.

TABLE 2

Glyphosate Tolerance in RT73 event compared to MON 88302

| Event | Glyphosate Rate (g ae/ha) | Crop Stage | 7-10 DAT % CHLR Avg | 14-21 DAT % GR Avg |
|---|---|---|---|---|
| RT73 | 0 | 4-6 leaf | 0.0 | 0.0 |
| RT73 | 450 | 4-6 leaf | 0.3 | 0.9 |
| RT73 | 900 | 4-6 leaf | 2.2 | 1.3 |
| RT73 | 1800 | 4-6 leaf | 4.7 | 5.3 |
| RT73 | 3600 | 4-6 leaf | 10.0 | 20.8 |
| RT73 | 450 | 1$^{st}$ flower | 0.6 | 0.8 |
| RT73 | 900 | 1$^{st}$ flower | 1.8 | 0.3 |
| RT73 | 1800 | 1$^{st}$ flower | 6.7 | 3.3 |
| RT73 | 3600 | 1$^{st}$ flower | 10.0 | 8.1 |
| MON88302 | 0 | 4-6 leaf | 0.0 | 0.0 |
| MON88302 | 450 | 4-6 leaf | 0.0 | 0.3 |
| MON88302 | 900 | 4-6 leaf | 0.7 | 0.7 |
| MON88302 | 1800 | 4-6 leaf | 1.7 | 0.0 |
| MON88302 | 3600 | 4-6 leaf | 1.7 | 0.3 |
| MON88302 | 450 | 1$^{st}$ flower | 0.0 | 0.0 |
| MON88302 | 900 | 1$^{st}$ flower | 0.3 | 0.8 |
| MON88302 | 1800 | 1$^{st}$ flower | 0.9 | 0.0 |
| MON88302 | 3600 | 1$^{st}$ flower | 4.7 | 1.1 |

Data on the days after planting to swath of canola comprising event RT73 compared to canola comprising event MON 88302 are provided in Table 3. Briefly, maturity was delayed significantly in the Genuity™ Roundup Ready® Canola system (RT73 event) at the 3600 g ae/ha rate at both the four to six leaf and first flower applications, likely a consequence of the crop injury. No delay in maturity was observed in the MON 88302 plants except that there was a significant shortening of maturity at the 1800 g ae/ha rate at the four to six leaf application staging.

TABLE 3

Days after Planting to Swath in RT73 event compared to MON 88302

| Variety | Application | Rate g/ha ae | Mean | Control | Delta - Days | P value |
|---|---|---|---|---|---|---|
| RT73 | 4-6 leaf | 450 | 103.6 | 103.8 | −0.20 | 0.45 |
| RT73 | 4-6 leaf | 900 | 103.6 | 103.8 | −0.25 | 0.36 |
| RT73 | 4-6 leaf | 1800 | 104.3 | 103.8 | 0.43 | 0.12 |
| RT73 | 4-6 leaf | 3600 | 104.7 | 103.8 | 0.83 | <0.05 |
| RT73 | 1$^{st}$ flower | 450 | 103.8 | 103.8 | 0.00 | 1.00 |

TABLE 3-continued

Days after Planting to Swath in
RT73 event compared to MON 88302

| Variety | Application | Rate g/ha ae | Mean | Control | Delta - Days | P value |
|---|---|---|---|---|---|---|
| RT73 | 1st flower | 900 | 104.2 | 103.8 | 0.33 | 0.21 |
| RT73 | 1st flower | 1800 | 104.3 | 103.8 | 0.50 | 0.06 |
| RT73 | 1st flower | 3600 | 104.7 | 103.8 | 0.83 | <0.05 |
| MON88302 | 4-6 leaf | 450 | 104.7 | 105.2 | −0.46 | 0.10 |
| MON88302 | 4-6 leaf | 900 | 105.2 | 105.2 | 0.04 | 0.90 |
| MON88302 | 4-6 leaf | 1800 | 104.5 | 105.2 | −0.67 | <0.05 |
| MON88302 | 4-6 leaf | 3600 | 105.2 | 105.2 | 0.00 | 1.00 |
| MON88302 | 1st flower | 450 | 105.1 | 105.2 | −0.08 | 0.75 |
| MON88302 | 1st flower | 900 | 104.7 | 105.2 | −0.42 | 0.12 |
| MON88302 | 1st flower | 1800 | 104.9 | 105.2 | −0.25 | 0.34 |
| MON88302 | 1st flower | 3600 | 105.0 | 105.2 | −0.17 | 0.53 |

Data on the seed moisture of canola comprising event RT73 compared to canola comprising event MON 88302 are provided in Table 4. Seed moisture was measured electronically when the individual plots were harvested. Seed moistures within each system were a comparison between the glyphosate rate sprayed and the unsprayed treatment. Seed moisture in the Genuity™ Roundup Ready® Canola system was higher at the 1800 g ae/ha and 3600 g ae/ha rates at both the four to six leaf and first flower crop stage applications. The increased seed moisture in these two treatments again reflects a delay in maturity, which is a result of crop injury previously described. No significant effects on seed moisture were observed in the MON 88302 plants.

TABLE 4

Seed Moisture in RT73 event compared to MON 88302

| Variety | Application | Rate g/ha ae | Treated Mean | Control | Delta % | P value |
|---|---|---|---|---|---|---|
| RT73 | 4-6 leaf | 450 | 7.6 | 7.3 | 0.4 | 0.41 |
| RT73 | 4-6 leaf | 900 | 7.7 | 7.3 | 0.4 | 0.35 |
| RT73 | 4-6 leaf | 1800 | 8.4 | 7.3 | 1.1 | <0.05 |
| RT73 | 4-6 leaf | 3600 | 9.8 | 7.3 | 2.5 | <0.05 |
| RT73 | 1st flower | 450 | 7.7 | 7.3 | 0.4 | 0.39 |
| RT73 | 1st flower | 900 | 8.0 | 7.3 | 0.7 | 0.09 |
| RT73 | 1st flower | 1800 | 8.3 | 7.3 | 1.0 | <0.05 |
| RT73 | 1st flower | 3600 | 9.3 | 7.3 | 2.0 | <0.05 |
| MON88302 | 4-6 leaf | 450 | 8.0 | 8.1 | −0.1 | 0.86 |
| MON88302 | 4-6 leaf | 900 | 8.0 | 8.1 | 0.0 | 0.96 |
| MON88302 | 4-6 leaf | 1800 | 8.0 | 8.1 | −0.1 | 0.87 |
| MON88302 | 4-6 leaf | 3600 | 7.9 | 8.1 | −0.2 | 0.69 |
| MON88302 | 1st flower | 450 | 8.2 | 8.1 | 0.2 | 0.72 |
| MON88302 | 1st flower | 900 | 8.3 | 8.1 | 0.2 | 0.60 |
| MON88302 | 1st flower | 1800 | 8.1 | 8.1 | 0.1 | 0.87 |
| MON88302 | 1st flower | 3600 | 8.4 | 8.1 | 0.3 | 0.44 |

Figure 2:
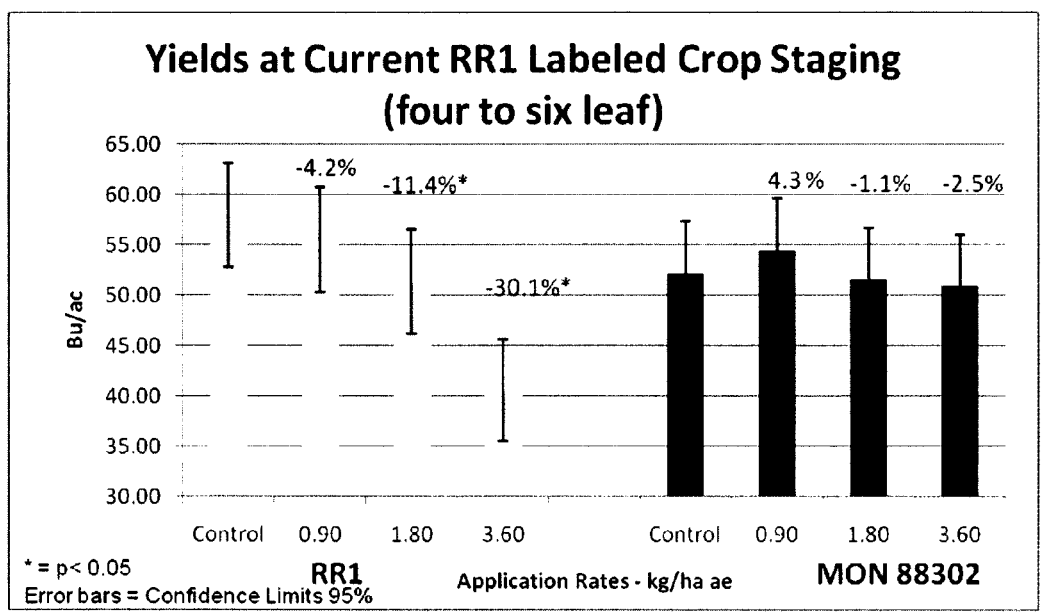
FIG. 2: Shows grain yield of RT73 event compared to MON 88302 when glyphosate is applied at the four to six leaf stage. RT73 is designated as RR1.
Figure 3:
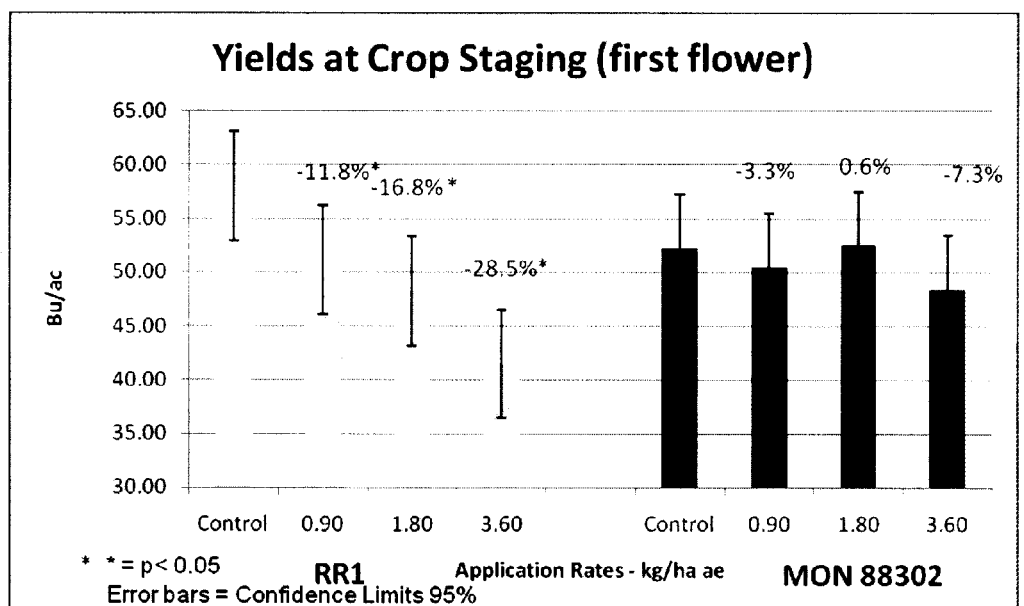
FIG. 3: Shows grain yield of RT73 event compared to MON 88302 when glyphosate is applied at first flower. RT73 is designated as RR1.

Data on the yield of canola comprising event RT73 compared to canola comprising event MON 88302 are provided in Table 5 and FIGS. 2 and 3. Yield comparisons were made between the different glyphosate rates and the unsprayed treatment for canola comprising each event. In the Genuity™ Roundup Ready® Canola system, significant yield reduction was observed at the 1800 and 3600 g ae/ha rates at both the four to six leaf and first flower applications and the 900 g/ha rate at the first flower application. No significant differences in yield were observed in the MON 88302 plants at any rate or timing.

TABLE 5

Yields in RT73 event compared to MON 88302

| Variety | Application | Rate g/ha ae | Treated Mean | Control | Delta bu/ac | P value |
|---|---|---|---|---|---|---|
| RT73 | 4-6 leaf | 450 | 56.0 | 58.0 | −2.0 | 0.45 |
| RT73 | 4-6 leaf | 900 | 55.6 | 58.0 | −2.4 | 0.36 |
| RT73 | 4-6 leaf | 1800 | 51.4 | 58.0 | −6.6 | <0.05 |
| RT73 | 4-6 leaf | 3600 | 40.6 | 58.0 | −17.4 | <0.05 |
| RT73 | 1st flower | 450 | 56.1 | 58.0 | −1.9 | 0.46 |
| RT73 | 1st flower | 900 | 51.2 | 58.0 | −6.8 | <0.05 |
| RT73 | 1st flower | 1800 | 48.2 | 58.0 | −9.8 | <0.05 |
| RT73 | 1st flower | 3600 | 41.5 | 58.0 | −16.5 | <0.05 |
| MON88302 | 4-6 leaf | 450 | 53.7 | 52.2 | 1.5 | 0.57 |
| MON88302 | 4-6 leaf | 900 | 54.4 | 52.2 | 2.2 | 0.40 |
| MON88302 | 4-6 leaf | 1800 | 51.6 | 52.2 | −0.6 | 0.82 |
| MON88302 | 4-6 leaf | 3600 | 50.9 | 52.2 | −1.3 | 0.61 |
| MON88302 | 1st flower | 450 | 52.3 | 52.2 | 0.1 | 0.98 |
| MON88302 | 1st flower | 900 | 50.4 | 52.2 | −1.7 | 0.49 |
| MON88302 | 1st flower | 1800 | 52.5 | 52.2 | 0.3 | 0.91 |
| MON88302 | 1st flower | 3600 | 48.4 | 52.2 | −3.8 | 0.14 |

The current labeled rate of glyphosate for the Genuity™ Roundup Ready® Canola system is 675 g ae/ha applied once or 450 g ae/ha applied twice. Applications can be made up to the six leaf stage. Rates for the MON88302 may be up to 1800 g ae/ha applied up to the first flower of the crop. The Genuity™ Roundup Ready® Canola system had 11.4% yield reduction at the proposed MON 88302 application rate of 1800 g ae/ha and 30% yield reduction at 2× the proposed rate (FIG. 2). These yield reductions were observed at the current labeled Genuity™ Roundup Ready® Canola crop application stage of four to six leaf. No significant yield reductions were observed in the MON 88302 plants. FIG. 3 shows the yields at the glyphosate rates and crop staging (first flower). There was a significant yield reduction in all rates shown for the Genuity™ Roundup Ready® Canola system at this later crop staging. No significant yield reductions were observed in the MON 88302 plants.

Example 3

Characterization of MON 88302 DNA Sequences

The DNA inserted into the genome of plant MON 88302 and the genomic sequence flanking the insert was characterized by detailed molecular analyses. These analyses included: sequencing the insert sequence, determining the insert number (number of integration sites within the genome), determining the copy number (number of copies of transgene DNA within one locus), assessing the integrity of the inserted gene cassette, and characterizing the flanking sequences.

Genomic DNA sequences flanking the transgene DNA insertion in event MON 88302 were determined using inverse thermal amplification as described in Ochman et al., 1990 (PCR Protocols: A guide to Methods and Applications, Academic Press, Inc.). Plant genomic DNA was isolated from non-transgenic Ebony and different transgenic events arising from the *Agrobacterium*-mediated transformation of *Brassica napus* described in Example 1. Tissue used for DNA isolation was produced under standard greenhouse conditions. Approximately 1 gram of young leaf tissue was combined with liquid nitrogen and ground to a fine powder using a mortar and pestle. DNA was extracted using a Nucleon™ PhytoPure™ Genomic DNA extraction kit (RPN8511, Amersham, Piscataway, N.J.) according to the manufacturer's protocol. After the final precipitation step, DNA from individual samples was resuspended in 0.5 ml of TE (10 mM Tris-HCl pH 8.0, 1 mM EDTA). This method can be modified by one skilled in the art to extract DNA from any tissue, including, but not limited to seed.

An aliquot of DNA from each sample was digested with restriction endonucleases selected based upon restriction analysis of the transgene DNA. After self-ligation of restriction fragments, thermal amplification was performed using primers designed from the transgene DNA sequence that would amplify sequences using either the ELONGASE® Amplification system (Cat. No. 10481-018, Invitrogen, Carlsbad, Calif.) or the Expand Long Template PCR System (Cat. No. 1681842, Roche Applied Science, Indianapolis, Ind.) extending away from the 5' and 3' ends of the transgene DNA. Amplicons produced from the reactions were separated by agarose gel electrophoresis and purified using a QIAGEN gel purification kit (Qiagen, Valencia, Calif.). The gel-purified amplicons were cloned into the pCR®-XL-TOPO® vector (Invitrogen, Carlsbad, Calif.) following the manufacturer's protocol. The resulting plasmids containing the event MON 88302 flanking genomic sequences were sequenced using standard DNA sequencing protocols. The genomic DNA adjacent to, or flanking, the 5' end of the transgenic DNA inserted into the genome is presented as SEQ ID NO: 3 ([C], see FIG. 1). The genomic DNA adjacent to the 3' end of the transgenic DNA inserted into the genome is presented as SEQ ID NO: 4 2([D], see FIG. 1). The segment of the expression cassette DNA that was fully integrated into the genomic DNA is presented as SEQ ID NO: 5 ([E], see FIG. 1).

Isolated DNA molecule sequences were compared to the transgene DNA sequence to identify the flanking sequence and the co-isolated transgene DNA fragment. Confirmation of the presence of the expression cassette was achieved by thermal amplification with primers designed based upon the deduced flanking sequence data and the known transgene DNA sequence. The wild type sequence corresponding to the same region in which the transgene DNA was integrated in the transformed line was isolated using primers designed from the flanking sequences in event MON 88302. The thermal amplification reactions were performed using the ELONGASE® Amplification system (Cat. No. 10481-018, Invitrogen, Carlsbad, Calif.). The flanking sequences in event MON 88302 and the Ebony wild type sequence were analyzed against multiple nucleotide and protein databases. This information was used to examine the relationship of the transgene to the plant genome and to evaluate the insertion site integrity. The flanking sequence and wild type sequences were used to design primers for TAQMAN endpoint assays used to identify the events.

Example 4

Event Specific Endpoint TAQMAN® Assays

This example describes an event specific endpoint TAQMAN® thermal amplification method developed to identify event MON 88302 in a sample. Examples of conditions useful with the event MON 88302 Specific Endpoint TAQMAN® method are as follows. Step 1: 18 megohm water adjusted for final volume of 10 µl. Step 2: 5.0 µl of 2× Universal Master Mix (dNTPs, enzyme, buffer) to a 1× final concentration. Step 3: 0.5 µl Primer-1 and Primer-2 Mix (resuspended in 18 megohm water to a concentration of 20 µM for each primer) to 1.0 µM final concentration (for example in a microcentrifuge tube, the following should be added to achieve 500 µl at a final concentration of 20 µM: 100 µl of Primer SQ20901 (SEQ ID NO: 9) at a concentration of 100 µM; 100 µl of Primer SQ23770 (SEQ ID NO: 10) at a concentration of 100 µM; 300 µl of 18 megohm water). Step 4: 0.2 µl Event 6-FAM™ MGB Probe PB10164 (SEQ ID NO: 11) to 0.2 µM final concentration. Step 5: 0.5 µl Internal Control Primer SQ2563 (SEQ ID NO: 17) and Internal Control Primer SQ2564 (SEQ ID NO: 18) Mix to 1.0 µM final concentration for each primer. Step 6: 0.2 µl Internal Control VIC™ Probe PB0751 (SEQ ID NO: 19) to 0.2 µM final concentration. Step 7: 3.0 µl Extracted DNA (template) for each sample with one each of the following comprising 1. Leaf Samples to be analyzed; 2. Negative control (non-transgenic DNA); 3. Negative water control (no template); 4. Positive control MON 88302 DNA. Step 8: Thermocycler Conditions as follows: One Cycle at 50° C. for 2 minutes; One Cycle at 95° C. for 10 minutes; Ten Cycles of 95° C. for 15 seconds then 64° C. for 1 minute with −1° C./cycle; Forty Cycles of 95° C. for 15 seconds then 54° C. 1 minute; final cycle of 10° C.

DNA molecules useful in the method are, for example, primers SQ20901 (SEQ ID NO: 9) and SQ23770 (SEQ ID NO: 10) and the 6FAM™-labeled oligonucleotide probe PB10164 (SEQ ID NO: 11). Other probes and primers may be designed based upon the sequences of the transgene insert and/or the flanking sequences provided herein. SQ20901 (SEQ ID NO: 9) and SQ23770 (SEQ ID NO: 10) when used in these reaction methods with PB10164 (SEQ ID NO: 11) produce an amplicon that is diagnostic for event MON 88302 DNA. The endpoint TAQMAN amplification method also confirms the integrity of the template DNA by amplification of FatA, a single-copy endogenous gene within Brassica napus. DNA molecules useful in the method are, for example, primers SQ2563 (SEQ ID NO: 17) and SQ2564 (SEQ ID NO: 18) and the VIC™-labeled oligonucleotide probe PB0751 (SEQ ID NO: 19). The controls for this analysis include a positive control from Brassica napus containing event MON 88302 DNA, a negative control from non-transgenic Brassica napus, and a negative control that contains no template DNA.

The endpoint TAQMAN® thermal amplification method was also used to develop zygosity assays for event MON 88302. A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wild type. This example describes an event specific endpoint TAQMAN® thermal amplification method developed to determine the zygosity of event MON 88302 in a sample. For this assay, a three primer assay was employed wherein primer SQ21948 (SEQ ID NO: 12) hybridizes and extends specifically from the inserted exogenous DNA, primer SQ22176 (SEQ ID NO: 13) hybridizes and extends specifically from the DNA flanking the 5' side of the inserted exogenous DNA, and primer SQ24635 (SEQ ID NO: 14) hybridizes and extends specifically from the DNA flanking the 3' side of the inserted exogenous DNA. The three primers are diagnostic for the event. In this example, primer SQ22176 (SEQ ID NO: 13) and primer SQ21948 (SEQ ID NO: 12) and the 6FAM™-labeled oligonucleotide probe PB4213 (SEQ ID NO: 15) are diagnostic when there is a copy of the inserted exogenous DNA. In this example, SQ22176 (SEQ ID NO: 13) and primer SQ24635 (SEQ ID NO: 14) and the VIC™-labeled oligonucleotide probe PB10787 (SEQ ID NO: 16) are diagnostic when there is no copy of the inserted exogenous DNA present in the genomic DNA, i.e. wild-type. When the three primers and two probes are mixed together in a PCR reaction with DNA extracted from a plant homozygous for event MON 88302, there is a fluorescent signal only from the 6FAM™-labeled oligonucleotide probe PB4213 (SEQ ID NO: 15) which is indicative of and diagnostic a plant homozygous for event MON 88302. When the three primers and two probes are mixed together in a PCR reaction with DNA extracted from a plant heterozygous for event MON 88302, there is a fluorescent signal from both the 6FAM™-labeled oligonucleotide probe PB4213 (SEQ ID NO: 15) and the VIC™-labeled oligonucleotide probe PB10787 (SEQ ID NO: 16) which is indicative of and diagnostic a plant heterozygous for event MON 88302. When the three primers and two probes are mixed together in a PCR reaction with DNA extracted from a plant which is null for event MON 88302 (i.e. wild type), there is a fluorescent signal from only the VIC™-labeled oligonucleotide probe PB10787 (SEQ ID NO: 16) which is indicative of and diagnostic a plant null for event MON 88302, i.e. wildtype. Examples of conditions useful with this method are as follows. Step 1: 18 megohm water adjusted for final volume of 10 µl. Step 2: 5.0 µl of 2× Universal Master Mix (dNTPs, enzyme, buffer) to a 1× final concentration. Step 3: 0.5 µl of Zygosity Primers SQ21948, SQ22176, SQ24635 (resuspended in 18 megohm water to a concentration of 20 uM for each primer) to a final concentration of 1.0 µM (for example in a microcentrifuge tube, the following should be added to achieve 500 µl at a final concentration of 20 uM: 100 µl of Primer 1 at a concentration of 100 µM; 100 µl of Primer 2 at a concentration of 100 µM; 300 µl of 18 megohm water). Step 4: 0.2 µl Zygosity 6-FAM™ MGB Probe PB4213 (SEQ ID NO: 15) (resuspended in 18 megohm water to a concentration of 10 µM) to 0.2 µM final concentration. Step 5: 0.5 µl Internal Control Primer SQ22176 (SEQ ID NO: 13) and Internal Control Primer SQ24635 (SEQ ID NO: 14) Mix (resuspended in 18 megohm water to a concentration of 20 uM for each primer) to 1.0 µM final concentration for each primer. Step 6: 0.2 µl Internal Control VIC™ Probe PB10787 (SEQ ID NO: 16) (resuspended in 18 megohm water to a concentration of 10 µM) to 0.2 µM final concentration. Step 7: 3.0 µl Extracted DNA (template) for each sample with one each of the following comprising 1. Leaf Samples to be analyzed; 2. Negative control (non-transgenic DNA); 3. Negative water control (no template); 4. Positive control MON 88302 DNA. Step 8: Thermocycler Conditions as follows: One Cycle at 50° C. for 2 minutes; One Cycle at 95° C. for 10 minutes; Ten Cycles of 95° C. for 15 seconds then 64° C. for 1 minute with −1° C./cycle; Thirty Cycles of 95° C. for 15 seconds then 54° C. 1 minute; final cycle of 10° C. A System 9700 or Stratagene Robocycler, MJ Engine DNA Engine PTC-225 thermocycler may be used. Other methods and apparatus are known to those skilled in the art that would be useful to produce amplicons for identifying the event MON 88302 DNA in a biological sample. When conducting thermal amplifications in the Eppendorf Mastercycler Gradient or MJ Engine, the thermocycler should be run in the calculated mode. When conducting thermal amplifications in the Perkin-Elmer 9700, the thermocycler should be set with the ramp speed at maximum.

Example 5

Identification of Event MON 88302 in any MON 88302 Breeding Activity

This example describes how one may identify event MON 88302 within the progeny of any breeding activity using plants comprising event MON 88302. DNA event primer pairs are used to produce an amplicon diagnostic for event MON 88302. An amplicon diagnostic for event MON 88302 comprises at least one junction sequence, provided herein as SEQ ID NO: 1 or SEQ ID NO: 2 ([A] and [B], respectively as illustrated in FIG. 1). SEQ ID NO: 1 ([A] of FIG. 1) is a nucleotide sequence corresponding to the junction of the flanking sequence with the 5' end of transgene insert (positions 762 through 821 of SEQ ID NO: 3 [C], see FIG. 1). SEQ ID NO: 2 ([B], see FIG. 1) is a nucleotide sequence corresponding to the junction of the flanking sequence with the 3' end of transgene insert (positions 313 through 372 of SEQ ID NO: 4 [D], see FIG. 1).

Event primer pairs that will produce a diagnostic amplicon for event MON 88302 include primer pairs designed using the flanking sequences (SEQ ID NO: 3 and 4) and the inserted transgenic DNA sequence (SEQ ID NO: 5). To acquire a diagnostic amplicon in which at least 40 nucleotides of SEQ ID NO: 1 is found, one would design a forward primer molecule based upon SEQ ID NO: 3 from bases 1 through 791 and a reverse primer molecule based upon the inserted expression cassette DNA sequence, SEQ ID NO: 5 from positions 1 through 4427 in which the primer molecules are of sufficient length of contiguous nucleotides to specifically hybridize to SEQ ID NO: 3 and SEQ ID NO: 5. To acquire a diagnostic amplicon in which at least 40 nucleotides of SEQ ID NO: 2 is found, one would design a forward primer molecule based upon the inserted expression cassette, SEQ ID NO: 5 from positions 1 through 4427 and a reverse primer molecule based upon the 3' flanking sequence, SEQ ID NO: 4 from bases 343 through 1250, in which the primer molecules are of sufficient length of contiguous nucleotides to specifically hybridize to SEQ ID NO: 4 and SEQ ID NO: 5. For practical purposes, one should design primers which produce amplicons of a limited size range, for example, between 100 to 1000 bases. Smaller (shorter polynucleotide length) sized amplicons in general may be more reliably produced in PCR reactions, allow for shorter cycle times, and be easily separated and visualized on agarose gels or adapted for use in endpoint TAQMAN®-like assays. Smaller amplicons can be produced and detected by methods known in the art of amplicon detection. In addition, amplicons produced using primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for event MON 88302 or progeny thereof is an aspect of the present invention. Any single isolated DNA polynucleotide primer molecule comprising at least 11 contiguous nucleotides of SEQ ID NO: 3, or its complement, that is useful in a DNA amplification method to produce an amplicon diagnostic for plants comprising event MON 88302 or progeny thereof is an aspect of the present invention. Any single isolated DNA polynucleotide primer molecule comprising at least 11 contiguous nucleotides of SEQ ID NO: 4, or its complement, that is useful in a DNA amplification method to produce an amplicon diagnostic for plants comprising event MON 88302 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for plants comprising event MON 88302 or progeny thereof is an aspect of the present invention.

An example of the amplification conditions for this analysis is described in Example 4 above. However, any modification of these methods or the use of DNA primers homologous or complementary to SEQ ID NO: 3 or SEQ ID NO: 4 or DNA sequences of the transgene insert (SEQ ID NO: 5) of event MON 88302 that produce an amplicon diagnostic for event MON 88302 is within the scope of the present disclosure. A diagnostic amplicon comprises a DNA molecule homologous or complementary to at least one transgene/genomic junction DNA (SEQ ID NO: 1 or SEQ ID NO: 2 or SEQ ID NO: 7 or SEQ ID NO: 8), or a substantial portion thereof.

An analysis for event MON 88302 in a sample may include a positive control from event MON 88302, a negative control from a comparable plant that is not event MON 88302 (for example, but not limited to, *Brassica napus*), and/or a negative control that contains no genomic DNA. A primer pair that will amplify an endogenous DNA molecule may serve as an internal control for the DNA amplification conditions. Any fragment of a sequence selected from sequences as set forth in SEQ ID NO: 3, SEQ ID NO: 4, or SEQ ID NO: 5 may be used as a DNA amplification primer for the production of an amplicon by the methods described in Example 4 and such an amplicon may be diagnostic for event MON 88302 when using event MON 88302 as template for such diagnostic amplification reaction. The use of these DNA primer sequences with modifications to the methods described in Example 4 are within the scope of the invention. The amplicon produced by at least one DNA primer sequence derived from SEQ ID NO: 3, SEQ ID NO: 4, or SEQ ID NO: 5 that is diagnostic for event MON 88302 is an aspect of the invention.

DNA detection kits, which contain at least one DNA primer of sufficient length of contiguous nucleotides derived from SEQ ID NO: 3, SEQ ID NO: 4, or SEQ ID NO: 5 and that when used in a DNA amplification method produces a diagnostic amplicon for a plant comprising event MON 88302 or its progeny, may thus be designed and are an aspect of the invention. A plant part or seed or commodity product that will produce an amplicon diagnostic for event MON 88302 when tested in a DNA amplification method is an aspect of the invention. The assay for the event MON 88302 amplicon can be performed by using any thermocycler or nucleic acid amplification system that can be used to produce an amplicon diagnostic of event MON 88302 as described herein.

A deposit of a representative sample of event MON 88302 seed disclosed above and recited in the claims has been made under the Budapest Treaty with the American Type Culture Collection (ATCC), 10801 University Boulevard, Manassas, Va. 20110. The ATCC accession number for this deposit is PTA-10955. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

We claim:

1. A method of producing a *Brassica napus* plant that tolerates application of glyphosate herbicide comprising:
   a) crossing a glyphosate tolerant *Brassica napus* plant comprising event MON 88302, a representative sample of seed comprising said event having been deposited under ATCC Accession Number PTA-10955, with a second *Brassica napus* plant, thereby producing seed;
   b) growing said seed to produce a plurality of progeny plants; and
   c) selecting a progeny plant that comprises event MON 88302.

2. The method of claim 1, wherein said selecting a progeny plant comprises treating said progeny plants with glyphosate and selecting a progeny plant that is tolerant to glyphosate.

3. The method of claim 1, wherein said selecting a progeny plant comprises identifying a progeny plant comprising a DNA molecule having a nucleotide sequence selected from the group consisting of SEQ ID NO: 1, SEQ ID NO: 2, SEQ ID NO: 3, SEQ ID NO: 4, SEQ ID NO: 7, and SEQ ID NO: 8.

4. The method of claim 1, wherein said second *Brassica napus* plant lacks tolerance to glyphosate herbicide.

5. A method of producing a *Brassica napus* plant that tolerates application of glyphosate herbicide comprising:
   a) selfing a glyphosate tolerant event *Brassica napus* plant comprising event MON 88302, a representative sample of seed comprising said event having been deposited under ATCC Accession Number PTA-10955, thereby producing seed;
   b) growing said seed to produce a plurality of progeny plants; and
   c) selecting a progeny plant that comprises event MON 88302.

6. The method of claim 3, wherein said selecting a progeny plant comprises identifying a progeny plant comprising a DNA molecule having the nucleotide sequence of SEQ ID NO: 1.

7. The method of claim 3, wherein said selecting a progeny plant comprises identifying a progeny plant comprising a DNA molecule having the nucleotide sequence of SEQ ID NO: 2.

8. The method of claim 3, wherein said selecting a progeny plant comprises identifying a progeny plant comprising a DNA molecule having the nucleotide sequence of SEQ ID NO: 3.

9. The method of claim 3, wherein said selecting a progeny plant comprises identifying a progeny plant comprising a DNA molecule having the nucleotide sequence of SEQ ID NO: 4.

10. The method of claim 3, wherein said selecting a progeny plant comprises identifying a progeny plant comprising a DNA molecule having the nucleotide sequence of SEQ ID NO: 7.

11. The method of claim 3, wherein said selecting a progeny plant comprises identifying a progeny plant comprising a DNA molecule having the nucleotide sequence of SEQ ID NO: 8.

12. The method of claim 1, wherein said second *Brassica napus* plant comprises tolerance to glyphosate herbicide.

13. The method of claim 5, wherein said selecting a progeny plant comprises treating said progeny plants with glyphosate and selecting a progeny plant that is tolerant to glyphosate.

14. The method of claim 5, wherein said selecting a progeny plant comprises identifying a progeny plant comprising a DNA molecule having a nucleotide sequence selected from the group consisting of SEQ ID NO: 1, SEQ ID NO: 2, SEQ ID NO: 3, SEQ ID NO: 4, SEQ ID NO: 7, and SEQ ID NO: 8.

15. The method of claim 5, wherein said selecting a progeny plant comprises identifying a progeny plant comprising a DNA molecule having the nucleotide sequence of SEQ ID NO: 1.

16. The method of claim 5, wherein said selecting a progeny plant comprises identifying a progeny plant comprising a DNA molecule having the nucleotide sequence of SEQ ID NO: 2.

17. The method of claim 5, wherein said selecting a progeny plant comprises identifying a progeny plant comprising a DNA molecule having the nucleotide sequence of SEQ ID NO: 3.

18. The method of claim 5, wherein said selecting a progeny plant comprises identifying a progeny plant comprising a DNA molecule having the nucleotide sequence of SEQ ID NO: 4.

19. The method of claim 5, wherein said selecting a progeny plant comprises identifying a progeny plant comprising a DNA molecule having the nucleotide sequence of SEQ ID NO: 7.

20. The method of claim 5, wherein said selecting a progeny plant comprises identifying a progeny plant comprising a DNA molecule having the nucleotide sequence of SEQ ID NO: 8.

21. The method of claim 3, wherein said second *Brassica napus* plant comprises tolerance to glyphosate herbicide.

* * * * *